(12) United States Patent
Isaka

(10) Patent No.: US 11,342,061 B2
(45) Date of Patent: *May 24, 2022

(54) EMOTIONAL WELLNESS MANAGEMENT SUPPORT SYSTEM AND METHODS THEREOF

(71) Applicant: Satoru Isaka, San Jose, CA (US)

(72) Inventor: Satoru Isaka, San Jose, CA (US)

(*) Notice: Subject to any disclaimer, the term of this patent is extended or adjusted under 35 U.S.C. 154(b) by 868 days.

This patent is subject to a terminal disclaimer.

(21) Appl. No.: 16/166,022

(22) Filed: Oct. 19, 2018

(65) Prior Publication Data

US 2019/0051399 A1     Feb. 14, 2019

Related U.S. Application Data

(63) Continuation-in-part of application No. 15/015,053, filed on Feb. 3, 2016, now Pat. No. 10,109,211.

(Continued)

(51) Int. Cl.
*A61B 5/00* (2006.01)
*G16H 20/70* (2018.01)
*A61B 5/16* (2006.01)
*G09B 5/06* (2006.01)
*G16H 10/60* (2018.01)
(Continued)

(52) U.S. Cl.
CPC ............ *G16H 20/70* (2018.01); *A61B 5/165* (2013.01); *G09B 5/06* (2013.01); *G16H 10/60* (2018.01); *G16H 20/30* (2018.01); *G16H 40/67* (2018.01); *G16H 80/00* (2018.01); *A61B 5/168* (2013.01); *G09B 19/00* (2013.01); *G16H 10/20* (2018.01); *H04L 63/10* (2013.01)

(58) Field of Classification Search
CPC combination set(s) only.
See application file for complete search history.

(56) References Cited

U.S. PATENT DOCUMENTS

2012/0101966 A1* 4/2012 van Coppenolle .... G06Q 30/06
706/20
2012/0130201 A1* 5/2012 Jain .......................... A61B 5/08
600/301

(Continued)

*Primary Examiner* — Masud Ahmed
(74) *Attorney, Agent, or Firm* — Intellectual Property Law Group LLP

(57) ABSTRACT

An emotional wellness management system and methods of managing emotional wellness, to help people interactively and iteratively manage and improve their daily processes of emotional wellness. The system comprises storage coupled to a controller for capturing, storing, retrieving, processing, updating and displaying information related to a user's psychological condition comprising user affects, influencers, and actions. A user interface device, coupled to the controller, configured to have a plurality of interactive interfaces to capture user inputs of states of user affects and influencers, provides action links for accessing resources in the user interface device, also providing visual feedback. The controller is configured to interface with at least one controller from a support network via a communication link, and able to capture, store, retrieve, process, update and display information related to user's psychological condition. The controllers from the support network are able to communicate with each other via a communication link.

20 Claims, 26 Drawing Sheets

Related U.S. Application Data

(60) Provisional application No. 62/176,510, filed on Feb. 20, 2015, provisional application No. 62/176,126, filed on Feb. 9, 2015.

(51) Int. Cl.
| | | |
|---|---|---|
| *G16H 80/00* | (2018.01) | |
| *G16H 20/30* | (2018.01) | |
| *G16H 40/67* | (2018.01) | |
| *H04L 29/06* | (2006.01) | |
| *G16H 10/20* | (2018.01) | |
| *G09B 19/00* | (2006.01) | |

(56) References Cited

U.S. PATENT DOCUMENTS

| | | | |
|---|---|---|---|
| 2014/0032234 A1* | 1/2014 | Anderson | G06Q 50/22 |
| | | | 705/2 |
| 2014/0121540 A1* | 5/2014 | Raskin | A61B 5/6898 |
| | | | 600/479 |
| 2015/0012288 A1* | 1/2015 | Riley | G06F 19/363 |
| | | | 705/2 |
| 2015/0040069 A1* | 2/2015 | Gunaratnam | G06F 3/04817 |
| | | | 715/834 |
| 2015/0088542 A1* | 3/2015 | Balassanian | G06F 19/363 |
| | | | 705/2 |
| 2015/0148621 A1* | 5/2015 | Sier | A61B 5/7267 |
| | | | 600/301 |

* cited by examiner

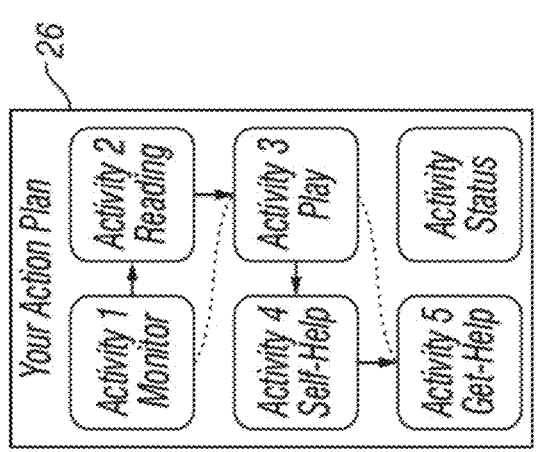
FIG. 13A
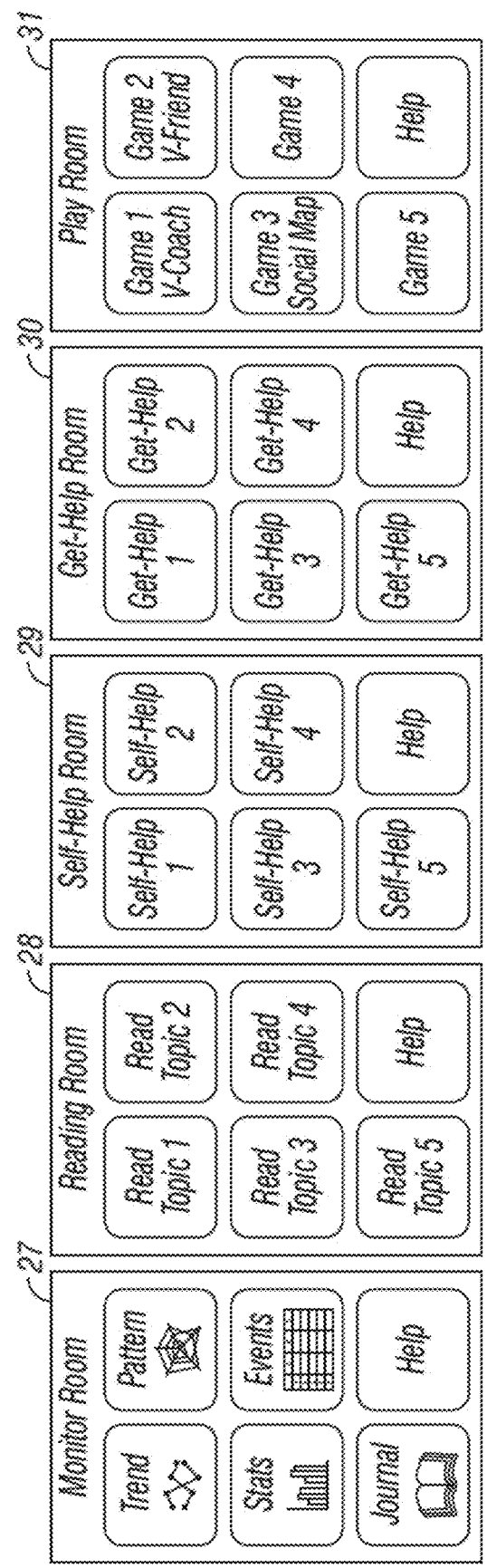
FIG. 13B
FIG. 13C
FIG. 13D
FIG. 13E
FIG. 13F

1401

| ID | Time Stamp | Counter | Fine | Tired | Anxious | Gloomy | Agitated | Depressed |
|---|---|---|---|---|---|---|---|---|
| Affect | 1507231230 | 0 | 0 | 0 | 0 | 0 | 0 | 0 |

1402

| ID | Time Stamp | Counter | PESI | PISI | PEPI | PIPI | PEMI | PIMI |
|---|---|---|---|---|---|---|---|---|
| Pxxl | 1507231230 | 0 | 0 | 0 | 0 | 0 | 0 | 0 |

1403

| ID | Time Stamp | Counter | NESI | NISI | NEPI | NIPI | NEMI | NIMI |
|---|---|---|---|---|---|---|---|---|
| Nxxl | 1507231230 | 0 | 0 | 0 | 0 | 0 | 0 | 0 |

1404

| ID | Time Stamp | Counter | Activity 1 | Activity 2 | Activity 3 | Activity 4 | Activity 5 | Activity 6 |
|---|---|---|---|---|---|---|---|---|
| Activity | 1507231230 | 0 | 0 | 0 | 0 | 0 | 0 | 0 |

*FIG. 14*

| ID | Time Stamp | Counter | Fine | Tired | Anxious | Gloomy | Agitated | Depressed |
|---|---|---|---|---|---|---|---|---|
| Affect | 1507250914 | 1 | 0 | 0 | 0 | 1 | 0 | 0 |

1501

| ID | Time Stamp | Counter | NESI | NISI | NEPI | NIPI | NEMI | NIMI |
|---|---|---|---|---|---|---|---|---|
| Nxxl | 1507250914 | 1 | 1 | 0 | 0 | 0 | 0 | 0 |

1502

| ID | Time Stamp | Counter | PESI | PISI | PEPI | PIPI | PEMI | PIMI |
|---|---|---|---|---|---|---|---|---|
| Pxxl | 1507250914 | 1 | 0 | 0 | 1 | 0 | 0 | 0 |

1503

| ID | Time Stamp | Counter | Statistics | Reading | Self-Help | Get-Help | Games | Device Help |
|---|---|---|---|---|---|---|---|---|
| Activity | 1507250914 | 1 | 0 | 1 | 0 | 0 | 0 | 0 |

| ID | Time Stamp | Counter | Fine | Tired | Anxious | Gloomy | Agitated | Depressed |
|---|---|---|---|---|---|---|---|---|
| Affect | 1510291355 | 100 | 21 | 12 | 45 | 7 | 15 | 0 |

*1602*

| ID | Time Stamp | Counter | NESI | NISI | NEPI | NIPI | NEMI | NIMI |
|---|---|---|---|---|---|---|---|---|
| Nxxl | 1510291355 | 100 | 40 | 5 | 16 | 13 | 21 | 5 |

*1603*

| ID | Time Stamp | Counter | PESI | PISI | PEPI | PIPI | PEMI | PIMI |
|---|---|---|---|---|---|---|---|---|
| Pxxl | 1510291355 | 100 | 5 | 5 | 41 | 31 | 11 | 7 |

*1604*

| ID | Time Stamp | Counter | Statistics | Reading | Self-Help | Get-Help | Games | Device Help |
|---|---|---|---|---|---|---|---|---|
| Activity | 1510291355 | 274 | 134 | 56 | 61 | 12 | 11 | 0 |

*FIG. 16A*

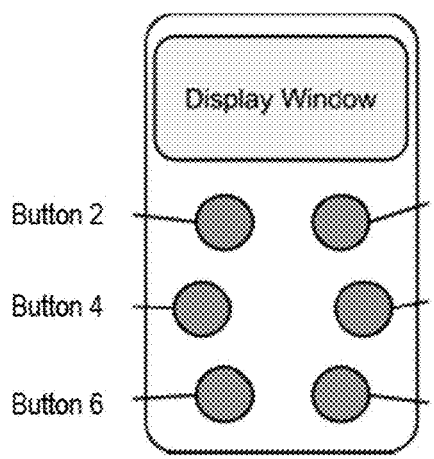
FIG. 17A
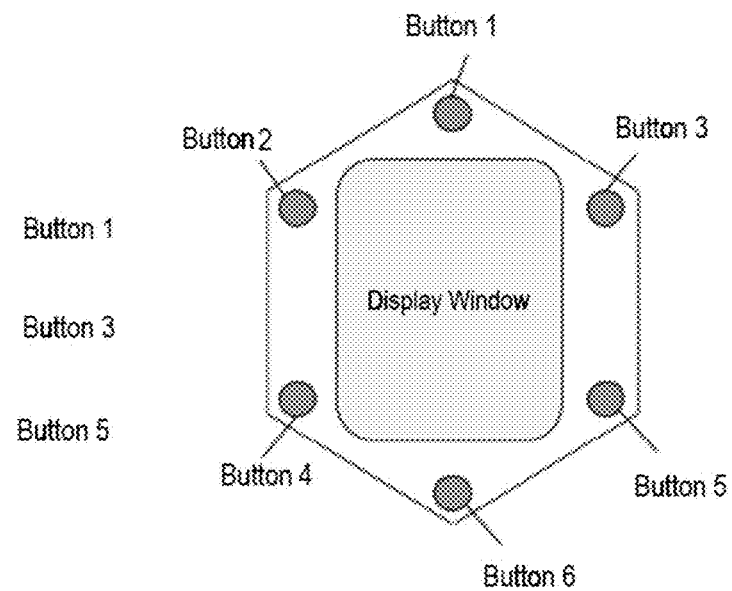
FIG. 17B
FIG. 17F
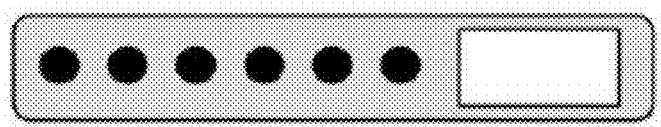
Inline (e.g. belt, bracelet)
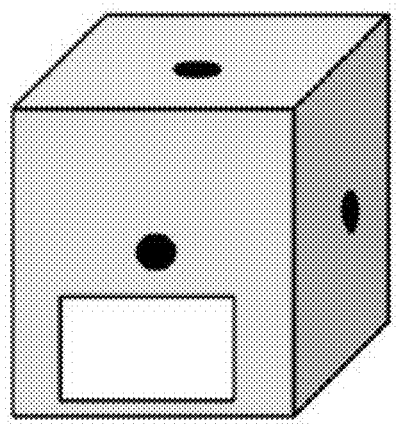
Cube (e.g. 6-facet dice)
FIG. 17E
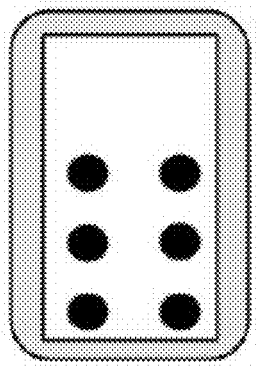
Box (e.g. handheld)
FIG. 17C
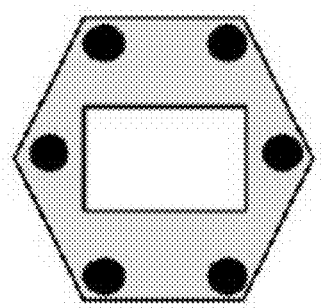
Hex (e.g. toy)
FIG. 17D

EMOTIONAL WELLNESS MANAGEMENT SUPPORT SYSTEM AND METHODS THEREOF

CROSS-REFERENCE TO RELATED APPLICATION

This application is a continuation-in-part of U.S. application Ser. No. 15/015,053, filed on Feb. 3, 2016, which is incorporated by reference in its entirety herein.

BACKGROUND OF THE INVENTION

1. Field of Invention

The exemplary embodiment(s) of the present invention relates to a support network and a support system for the user. More specifically, the exemplary embodiment(s) of the present invention relates to a support network and a support system for emotional wellness management.

2. Background

The global economic cost of mental health exceeds $2.5 trillion annually and is rapidly growing, reaching $6 trillion by 2030, more than the costs of cancer, diabetes, and respiratory diseases put together, according to the World Economic Forum and Harvard School of Public Health. Current medical care systems predominantly focus on physical health by treating diseases and injuries, leaving mental health up to individuals. Mental health affects everyone yet it is invisible. Its social and perceived stigma, coupled with insufficient care is giving mental health an undesirable nickname, "an orphan of healthcare."

Currently, four types of solutions exist: psychotherapy, support and peer groups, spiritual and faith-based healing and self-help. Psychotherapies including pharmacotherapies are designed for people with pathological conditions. The access is limited due to a shortage of qualified therapists and gaps in insurance coverage. Support and peer groups, as well as spiritual and faith-based healing are organized arbitrarily and are non-systematic. There is an increasing number of technology-based solutions in the form of self-help software; however, their efficacy is unproven.

Current technology-based solutions for physiological problems, such as illnesses and injuries follow the traditional medical practice of diagnosing symptoms and applying treatments based on diagnosis. Technology-based solutions for psychological problems such as stress, anxiety and depression follow the same approach as the traditional practice of symptom diagnosis and treatments. Unfortunately, mental health is different from physical health problems. The effects and symptoms are inconsistent and vary significantly with individuals, and often asymptomatic, meaning that symptoms do not always manifest themselves. This is why diagnosing and treating mental health is difficult. The traditional practice of treatments-on-symptoms approach does not always provide consistent and sustainable solutions for mental health problems. The current technology-based solutions need improvement.

Mental health is not a matter of applying treatments to symptoms. It is a process, a life-long process of becoming aware of and making choices for mental and social well-being. Emotion is a core driver of human behavior and is at the center of mental and social well-being. Emotional wellness is a critical component of predictive and preventive care for mental health, just as important as diet and exercise for physical health.

Because emotional wellness is a process, in order to achieve systematic improvement in a process, a specially designed system is needed to execute and improve the process iteratively. No practical system or method has been invented for emotional wellness as a process function that supports iterative process improvement. Further, there exists no structured representation of causal factors for emotional wellness. Therefore, there is a need for an emotional wellness management system to help users manage and improve their daily process of emotional wellness by providing a feedback loop with adaptive actions for continual monitoring and improvement in emotional wellness. There is also a need for structured representation of casual factors for emotional wellness.

Currently, there is a system and method for emotional wellness that comprise of capturing user affect and influencers using six buttons; however, this system and method can be broadened to capture user affect and user influencers that are less than six or more than six and the interactive interface can be other than buttons.

There is a need for software that converts data captured about user affect and influencers in graph form into text data. This function helps users understand what the graphs mean. There is also a need to integrate the data collected from the user with medical professions' databases, i.e. electronic medical records. Further, there is a need for a method of wireless data transfer by using Bluetooth or near-field communication ("NFC"). Lastly, there is a need to broaden the system of capturing user affect and user influencer beyond or less than a number of six and to have other types of interactive interfaces besides buttons.

SUMMARY

According to an embodiment of the present invention, there is an iterative emotional wellness management system which uses a user interface ("UI") device having a plurality of interactive interfaces to capture user inputs directed to states of user affects and user influencers, and to provide action links. The user interface communicates with at least one other UI in a support network via a communication link. The plurality of user interfaces in the support network communicates with each other via a communication link. The system comprises a user controller that is coupled to the user interface device, the user controller being able to capture, store, retrieve, process, update and display information related to and comprising user affects, user influencers, and actions. The system further comprising a storage coupled to the controller and configured to have a user affect database, user influencer database and a user activity database. The user controller being able to communicate with at least one controller in the support network. The controller in the support network also being able to capture, store, retrieve, process, update and display information related to and comprising user affect, user influencers, and actions of the user. There is an auto-narrative function that converts a graphical influencer diagram and a user affect diagram to text data on the UI device.

In further embodiments of the present invention, there is an auto-narrative function that converts a graphical influencer diagram representing user influencers over a predefined period of time and a user affect diagram representing user affect over a predefined period of time to text data on the user interface device.

According to another embodiment of the present invention, there is a method of managing emotional wellness in a system comprising a user interface ("UI") device, a user storage and a user controller. The method includes capturing at least one user affect at least partially representing user's psychological condition from the UI device. One or more databases are updated in accordance with the at least one user affect. A user influencer at least partially representing categorical attributes that influence user's affect from the UI device is captured, and the one or more databases are updated in accordance with the at least one user influencer. The user controller connects to at least one other user interface device in a support network. The plurality of user interface devices in a support network connects to each other via a communication link. Action links are generated to the user for accessing resources in the UI device in response to the one or more databases. The method steps are iterated to obtain a desired state of emotional wellness.

According to an embodiment of the present invention, there is an article of manufacture for use in a digital processing system for managing emotional wellness. The article of manufacture comprises a digital processing system usable medium having readable program code embodied in the medium, the program code comprising: capturing at least one user affect at least partially representing user's psychological condition from a user interface ("UI") device; updating one or more databases in accordance with the at least one user affect; capturing at least one user influencer at least partially representing categorical attributes that influence user's affect from the UI device; updating one or more databases in accordance with the at least one user influencer; connecting to at least one other UI device in a support network; generating and displaying action links to a user for accessing resources in the UI device in response to the one or more databases; and iterating the above steps.

According to an embodiment of the present invention, there is an iterative emotional wellness management support system which uses a user interface ("UI") device comprising at least two interactive interfaces to capture user inputs directed to states of user affect and user influencers, and to provide action links.

According to an embodiment of the present invention, there are methods to capture at least two user affect and at least two user influencers.

According to an embodiment of the present invention, there are alternative methods to capture user affect and user influencers without using buttons.

According to an embodiment of the present invention, there are alternative methods to display the user affect and user influencers as a text data as well as a variety of graph types.

According to an embodiment of the present invention, more than one electronic device can hold the user's data and there are methods to transfer and share the user's captured data between electronic devices.

Additional features and benefits of the exemplary embodiment(s) of the present invention will become apparent from the detailed description, figures and claims set forth below.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

FIGS. 13A-13F illustrate broader illustrations of action links with six buttons in accordance with embodiments of the present invention.

FIG. 14 illustrates default data structure of user affect positive influencers, negative influencers, and user activities in accordance with one embodiment of the present invention.

FIGS. 15A and 15B illustrate when new data is captured in accordance with an embodiment of the present invention.

FIG. 16A illustrates accumulated data sets for the first 100 entries and FIG. 16B illustrates an influencer diagram in accordance with embodiments of the present invention.

FIGS. 17A-17F illustrates various forms of a six-button device in accordance with embodiments of the present invention.

FIGS. 17K-17N illustrates customizable interactive interfaces, non-button methods to select an arbitrary number of options in accordance with embodiments of the present invention.

DETAILED DESCRIPTION OF SPECIFIC EMBODIMENTS

Figure 1A:
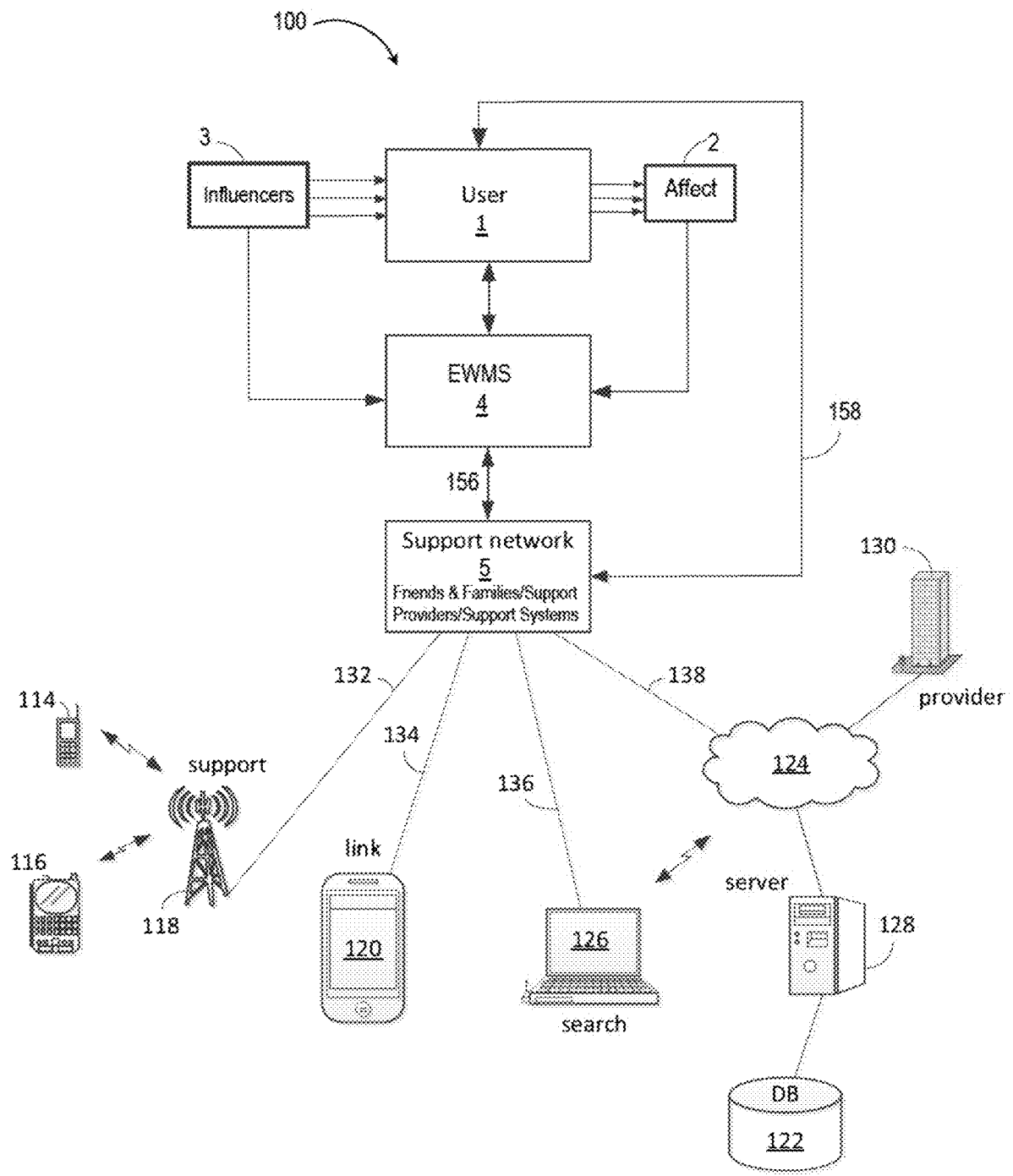
FIG. 1A is a block diagram illustrating a system view of how the user regulates, manages and improves affect in accordance with one embodiment of the present invention.

Exemplary embodiment(s) of the present invention is described herein in the context of a system, method, and article of manufacture for managing emotional wellness.

Those of ordinary skills in the art will realize that the following detailed description of the exemplary embodiment(s) is illustrative only and is not intended to be in any way limiting. Other embodiments will readily suggest themselves to such skilled persons having the benefit of this disclosure. Reference will now be made in detail to implementations of the exemplary embodiment(s) as illustrated in the accompanying drawings. The same reference indicators will be used throughout the drawings and the following detailed description to refer to the same or like parts.

In the interest of clarity, not all of the routine features of the implementations described herein are shown and described. It will, of course, be understood that in the development of any such actual implementation, numerous implementation-specific decisions may be made in order to achieve the developer's specific goals, such as compliance with application- and business-related constraints, and that these specific goals will vary from one implementation to another and from one developer to another. Moreover, it will be understood that such a development effort might be complex and time-consuming, but would nevertheless be a routine undertaking of engineering for those of ordinary skills in the art having the benefit of embodiment(s) of this disclosure.

Unless otherwise defined, all terms (including technical and scientific terms) used herein have the same meaning as commonly understood by one of ordinary skills in the art to which the exemplary embodiment(s) belongs. It will be further understood that terms, such as those defined in commonly used dictionaries, should be interpreted as having a meaning that is consistent with their meaning in the context of the relevant art and this exemplary embodiment(s) of the disclosure.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. The term "system" is used generically herein to describe any number of components, elements, sub-systems, devices, routers, networks, computer and/or communication devices or mechanisms, controller, storage, user interface, or combinations of components thereof. The term "computer" includes a processor, memory, and buses capable of executing instruction wherein the computer refers to one or a cluster of computers, personal computers, workstations, mainframes, or combinations of computers thereof.

Emotional wellness is a critical component of predictive and preventive care for mental health, just as important as diet and exercise are for physical health. Emotional wellness is not a matter of applying treatments to symptoms, but a lifelong process of being aware and making choices. Because emotional wellness is a process, in order to achieve systematic improvement, a specially designed system is needed. Embodiments of the present invention are directed to the system and method of helping people manage and improve their process of emotional wellness.

A user can view a graph on a screen but not understand what the graph means and what the recommendation may be. What a user needs is to view a graph on the screen, touch a help button, and then see a new page with details and meanings about the graph in descriptive text. The forms and types of data do not need to be fixed. Instead, there are alternative methods to display the user affect and influencers as text data as well as a variety of graph types.

FIG. 1A is a block diagram illustrating a system view 100 of how an embodiment of the present invention helps the user 1 regulate, manage and improve affect 2 which is the experience of feeling or emotion. Influencers 3 are categorical factors influencing the user affect 2. The Emotional Wellness Management System (EWMS) 4 captures affect 2 and influencers 3, and generates action links to the user 1, providing a feedback mechanism for the user 1 and iteratively improving the process of emotional wellness. In addition, the EWMS 4 communicates with a support network 5 that includes friends and families, support providers such as physicians and therapists, and support systems such as telemedicine and mobile application systems. Such communication with the support network 5 can be executed via direct links, emails, text messaging and phone via local network, wireless, Bluetooth or any other network and communication systems.

As illustrated in FIG. 1A, EWMS 4 and the support network 5 communicate via system link 156. Support network 5 and the user 1 communicate via link 158. Support network 5 may be coupled to Internet, wide area network ("WAN"), or virtual private network ("VPN"), hereinafter referred to as Internet 124 via connection 138. Internet, WAN, or VPN provides network communication between support network 5 and network devices such as server 128 and service provider(s) 130. Support network 5 is coupled via connections with various devices, such as laptop 126, handheld/mobile devices including smartphone 120, and other wireless devices via connections 132-136. Cell tower 118 is coupled to various devices such as cellular phone 114 or other mobile and handheld devices 116, tablets and/or iPad® via wireless communication. Handheld devices include smartphones, such as iPhone®, BlackBerry®, Android®, and so on. Similarly, the user's interface device may be configured for connection with the EWMS 4 and the support network 5, through various similar network and communication systems. It should be noted that the underlying concept of the exemplary embodiment(s) of the present invention would not change if one or more blocks (or devices) were added to or removed from FIG. 1A.

Figure 1B:
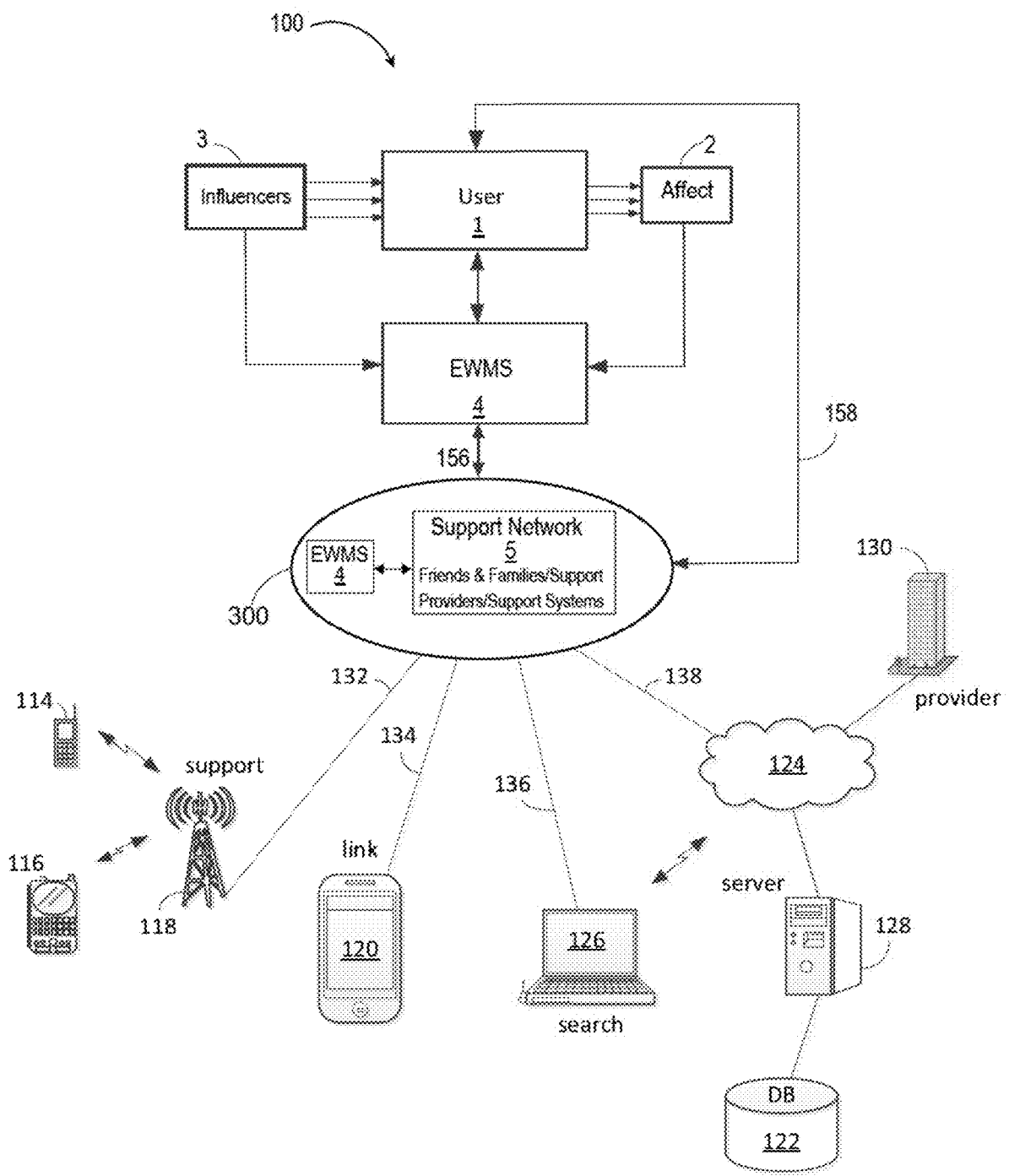
FIG. 1B is a block diagram illustrating a system view of an emotional wellness management support system and methods in accordance with one embodiment of the present invention.

FIG. 1B is a block diagram illustrating a system view of an emotional wellness management support system and methods in accordance with one embodiment of the present invention. To increase the flexibility in an embodiment is to transfer and share the captured data between electronic devices. The users of the support network 5 can have their own EWMS 4 enabled devices. This arrangement is referenced as 300 in FIG. 1B. For example, a physician or other medical profession can use a mobile application system that implements the EWMS 4 to capture a user's affect and influencer data on behalf of the user by talking to the user directly in the office or via link 158.

The user 1 and physician can both possess the EWMS 4 enabled devices. For example, a user brings their EWMS 4 enabled device with the captured data to a physician in the support network 5. The physician has a separate EWMS 4 enabled device but without data. The user's EWMS 4 can send the data to the physician's EWMS 4 via system link 156. In this example, the support network 5 includes the second set of EWMS 4 and the system link 156 becomes a communication link between the user's EWMS 4 device and the physician's EWMS 4 device. The system link 156 connects two or more EWMS 4 devices by wireless communication methods such as Bluetooth, near-field communication (NFC), infrared, radio frequency, or other wireless communication means. In addition, the system link 156 can also be a visual code display and reader pair, where one EWMS device displays a visual code such as bar codes and QR (quick-response) codes, while the other EWMS reads such codes to receive information. For example, QR codes serve as the system link 156 (the communication link) between EWMS 4 devices.

Figure 2A:
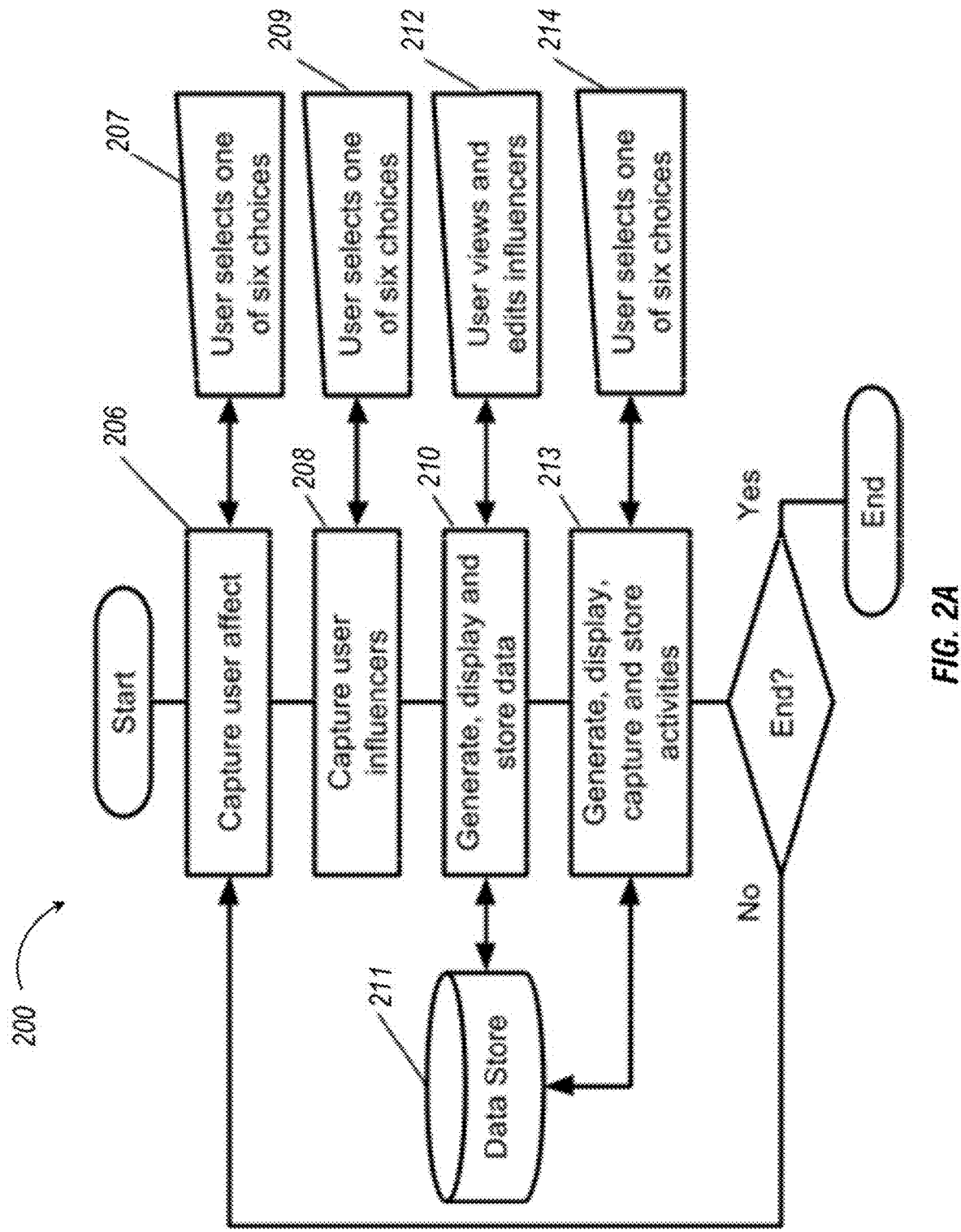
FIG. 2A is a system flowchart illustrating how the emotional wellness management system (EWMS) interacts with a user in accordance with one embodiment of the present invention.

FIG. 2A is a system flowchart 200 illustrating how the emotional wellness management system (EWMS) 4 interacts with a user in accordance with embodiments of the present invention. First, the system captures user affect by displaying a set of six selections of affect with brief descriptions. The user selects one of six choices 207 and the system captures the selection 206. Next, the system captures user influencers by displaying a set of six selections of negative influencers with brief descriptions. The user selects one of six choices 209 and the system captures the selection 208. The system repeats the process of steps 208 and 209, but this time displaying a set of six selections of positive influencers with brief descriptions. The user selects one of six choices 209 and the system captures the selection 208.

Once the affect and negative/positive influencers are captured, the system stores the data to a data store 211, retrieves previous data from the data store 211, and generates and displays the affect and influencer diagrams 210. The user views and optionally edits the influencer diagrams 212. Lastly, the system generates beneficial activities that connect the user to the support network, and displays a set of six buttons of action links with brief descriptions 213. The user selects one of six choices to select an activity 214, and the system captures the choice and stores it in the data store 211. The process repeats when the user returns to the system. In an embodiment, the data store 211 is configured to comprise one or more databases including a user affect database, a user influencer database and a user activity database.

Figure 2B:
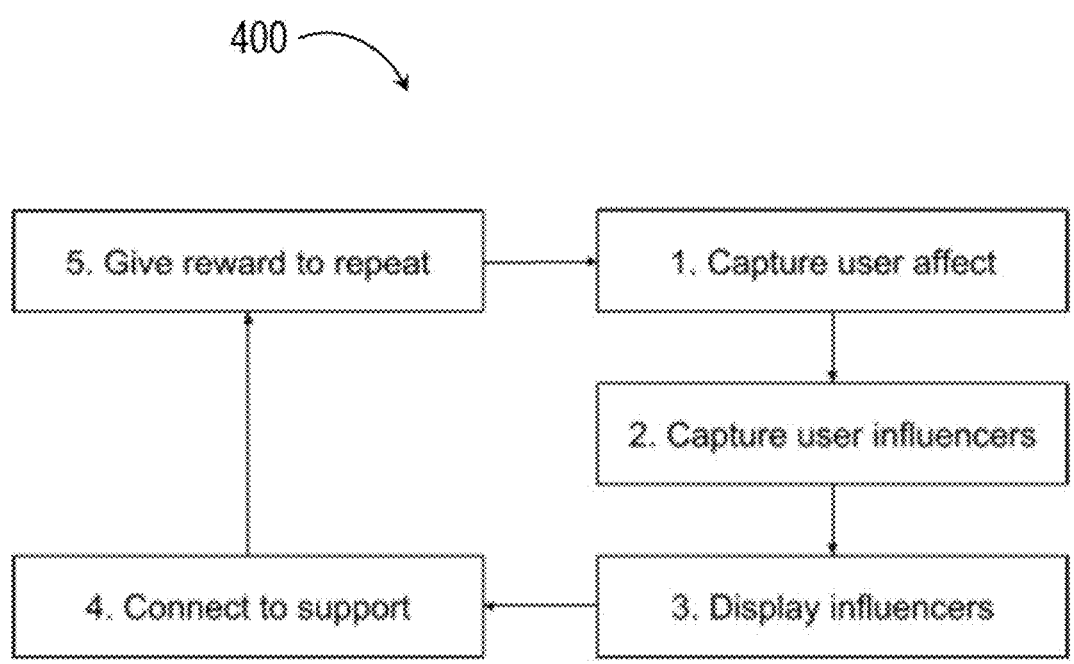
FIG. 2B is a system flowchart illustrating how the emotional wellness management support system and methods interacts with a user in accordance with one embodiment of the present invention.
Figure 3:
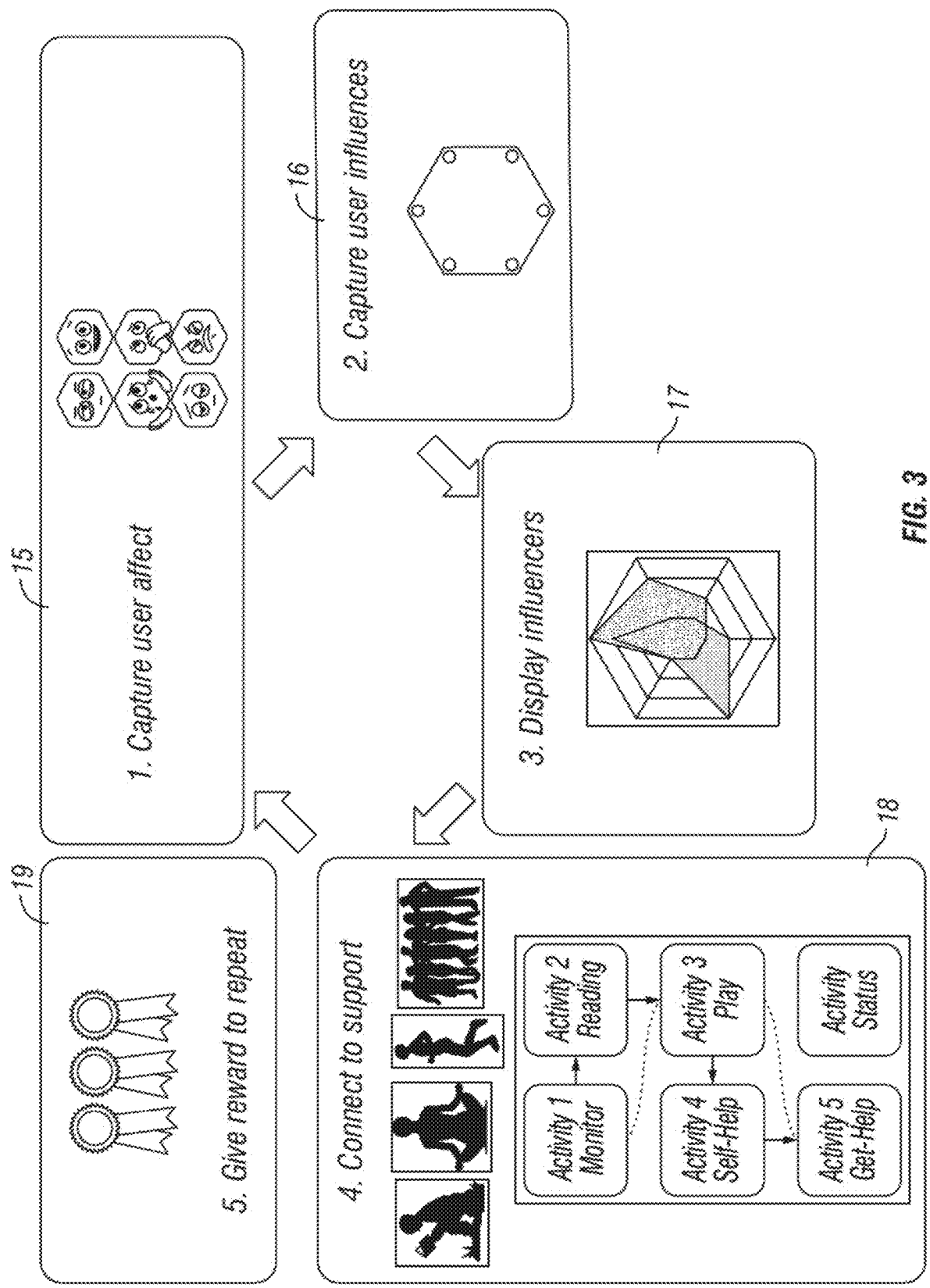
FIG. 3 illustrates the five-step emotional wellness management process in accordance with one embodiment of the present invention.

FIG. 2B is a system flowchart 400 illustrating how the emotional wellness management support system 4 interacts with a user in accordance with one embodiment of the present invention. The emotional wellness management support system helps people assist others in managing and improving their emotional wellness. This embodiment follows a similar five-step process as illustrated in FIG. 3, but without exemplifying images as shown in capture user affect 15, capture user influencers 16, display influencers 17, and connect to support 18. This shows that the present embodiments are inclusive, not exclusive to the utility of the present invention. As shown in FIG. 2B, in this embodiment, the EWMS 4 follows the steps of 1) capture user affect, 2) capture user influencers, 3) display influencers, 4) connect to support, and 5) give reward to repeat.

FIG. 3 illustrates the five-step emotional wellness management process, depicting an iterative nature of the emotional wellness management system in accordance with one embodiment of the present invention. Because emotional wellness is a process, in order to achieve systematic improvement in the process, a specially designed system is needed. The present invention is the specially designed system that facilitates the process by capturing user affect 15, capturing user influencers 16, displaying the affect and influencer diagrams 17, and connecting the user to a support network 18. The user repeats the cycle to iterate the process of emotional wellness. To further encourage the user to repeat the process, the system provides a reward to the user 19. The reward provided may include points that can be exchanged for goods and services, or discount privileges for goods and services. The user interface device is configured for capturing user affect 15, capturing user influencers 16, and displaying the affect and influencer diagrams 17.

Figure 4:
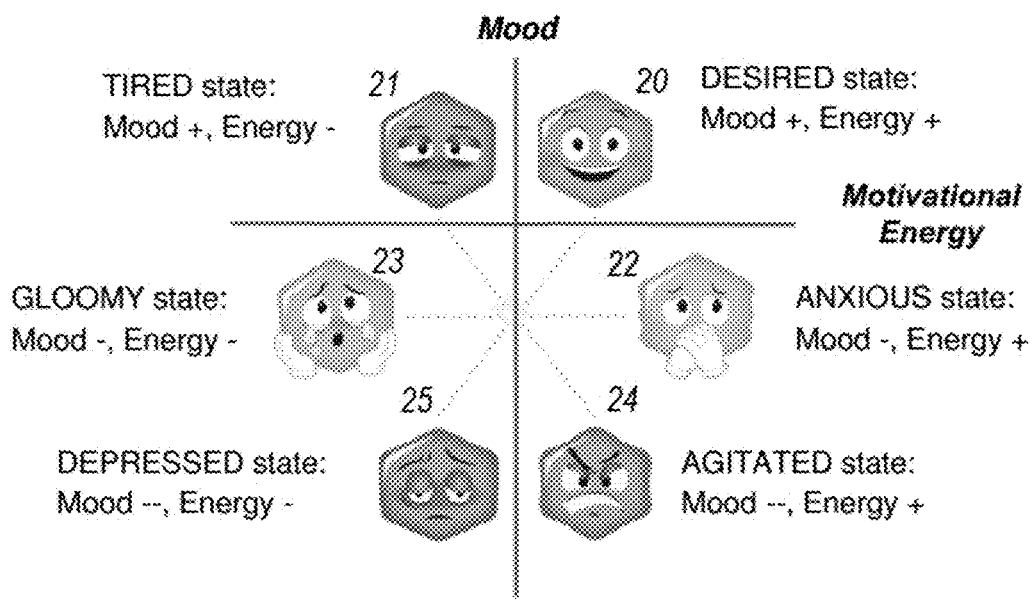
FIG. 4 illustrates six affect states in accordance with one embodiment of the present invention.

FIG. 4 illustrates six affect states in accordance with one embodiment of the present invention. In psychology, affect is commonly represented in two variables: valence and arousal. In an embodiment of the present invention a different method is used to represent affect: mood and motivational energy as shown in FIG. 4. In psychology, valence is a two-value variable, indicating either attractiveness (positive valence) or aversiveness (negative valence) of an event, object, or situation. In an embodiment of the present invention a term MOOD is used to represent valence but with three values instead of two: positive, negative, and severely negative.

In psychology, arousal is a state of being reactive to stimuli. However, arousal does not indicate motivation or energy. In an embodiment of the present invention a term MOTIVATIONAL ENERGY is used to represent subjectively assessed energy levels by a user with two values: high and low. By representing motivational energy in the x-axis and mood in the y-axis, in an embodiment of the present invention a two-dimensional map of user affect is constructed. This x-y plane is referred as the emotional wellness map. Because mood is three-valued and motivational energy is two-valued, the emotional wellness map has six regions: positive mood and positive energy 20 (referred as DESIRED state), positive mood and negative energy 21 (TIRED state), negative mood and positive energy 22 (ANXIOUS state), negative mood and negative energy 23 (GLOOMY state), severely negative mood and positive energy 24 (AGITATED state), and severely negative mood and negative energy 25 (DEPRESSED state).

Figure 5A:
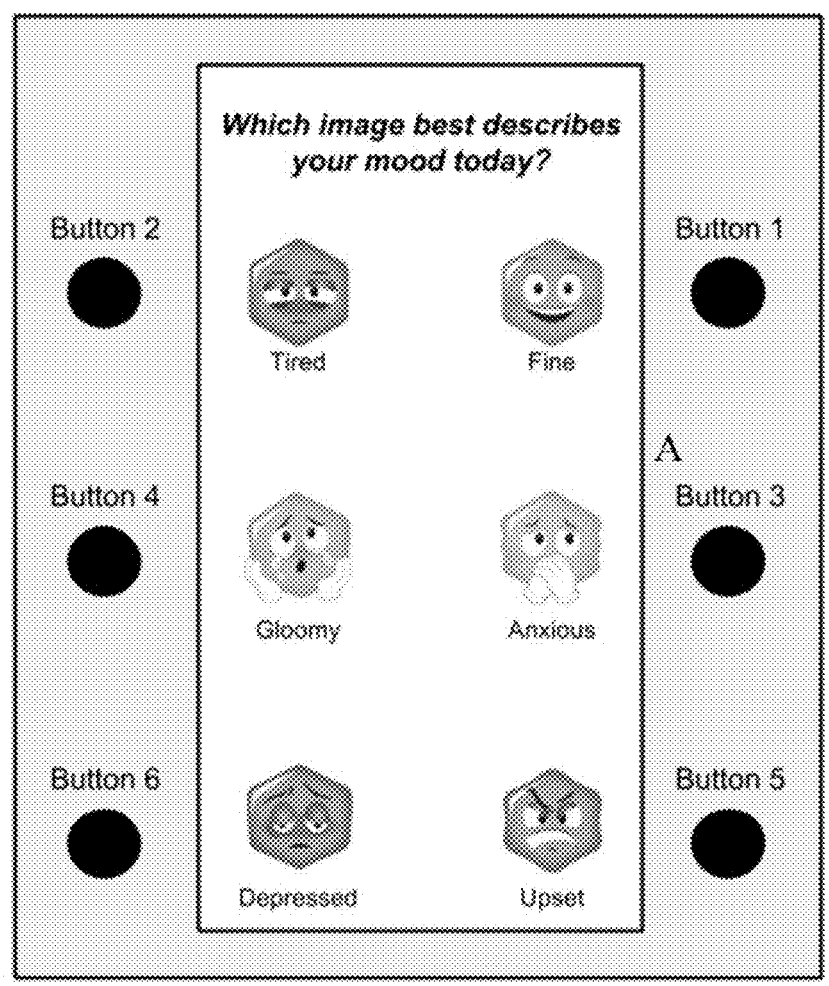
FIG. 5A illustrates how the EWMS captures user affect in accordance with one embodiment of the present invention.

FIG. 5A illustrates how the system captures user affect in accordance with one embodiment of the present invention. There are multiple methods of capturing user affect. In preferred embodiments of the present invention, the user presses one of six buttons or iconized images as shown in FIG. 5 on the user interface ("UI" device). The user touches an image or button on the user interface device to select one of six affect states: DESIRED (fine), TIRED, ANXIOUS, GLOOMY, AGITATED (upset), and DEPRESSED. Alternatively, other images, photographs, audio sounds or text can be used.

Another method of selection is to tap on a device using patterns. Each pattern corresponds to one of six affect states. For example, one tap represents the DESIRED state, two taps TIRED, three taps ANXIOUS, four taps GLOOMY, many rapid tapping can represent AGITATED, a few slow tapping can represent DEPRESSED state. This method can be implemented and is useful on a small electronic device similar to a watch or fitness bands with small or no display screen.

Figure 5B:
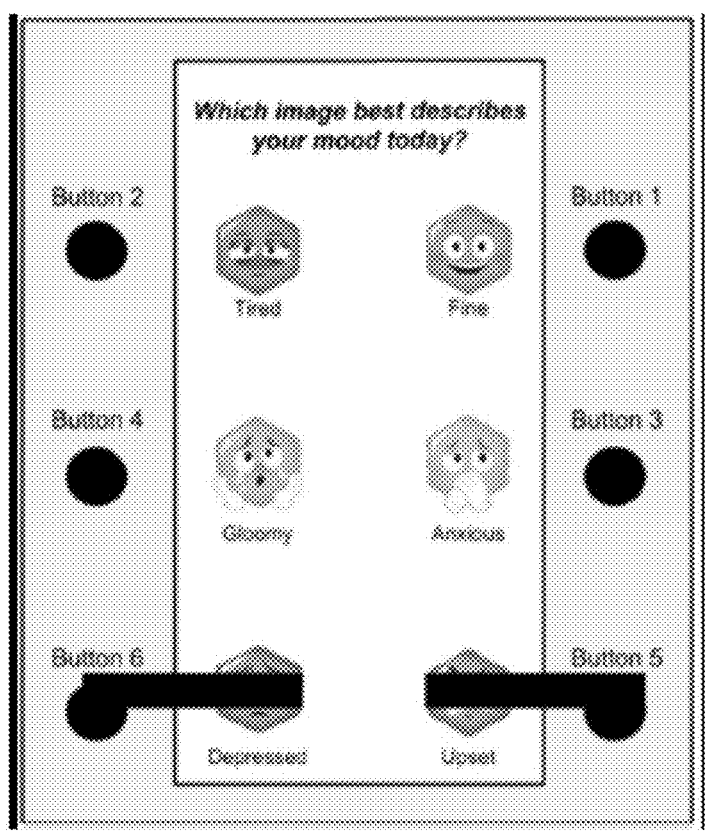
FIG. 5B illustrates how two user affect can be eliminated to make user affect equal four in accordance with one embodiment of the present invention.
Figure 5C:
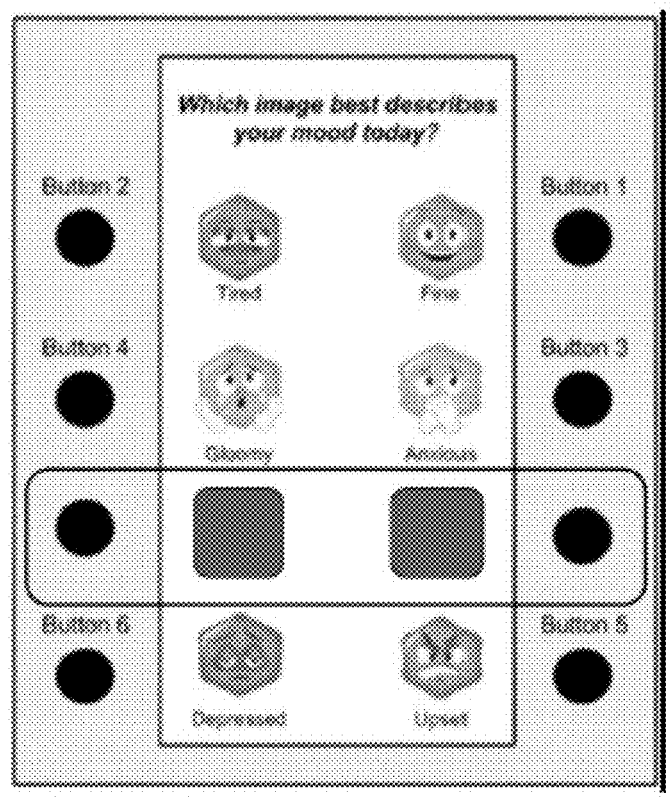
FIG. 5C illustrates how two user affect can be added to make user affect equal eight in accordance with one embodiment of the present invention.

FIG. 5B illustrates how two user affect can be eliminated to make it n=4 in accordance with one embodiment of the present invention. The number of user affect can be reduced by eliminating one or more user affect. As illustrated in FIG. 5B, anxious and depressed can be removed but tired, fine, gloomy and upset can remain. FIG. 5C illustrates how two user affect can be added to make it n=8 in accordance with one embodiment of the present invention.

There are many states of user affect. One state of a user affect can comprise of mood and motivational energy. However, other states can be contemplated. One embodiment describes three levels of mood: positive, negative, and severely negative. This embodiment describes two levels of motivational energy: high and low. However, the number of levels in motivational energy and mood can be changed without affecting the utility of the present invention. For example, mood state can be changed to two-valued level: positive and negative or changed to four-valued level. This is a choice by system designers who determine the appropriate levels of granularity in the mood and motivational energy dimensions.

Figure 6A:
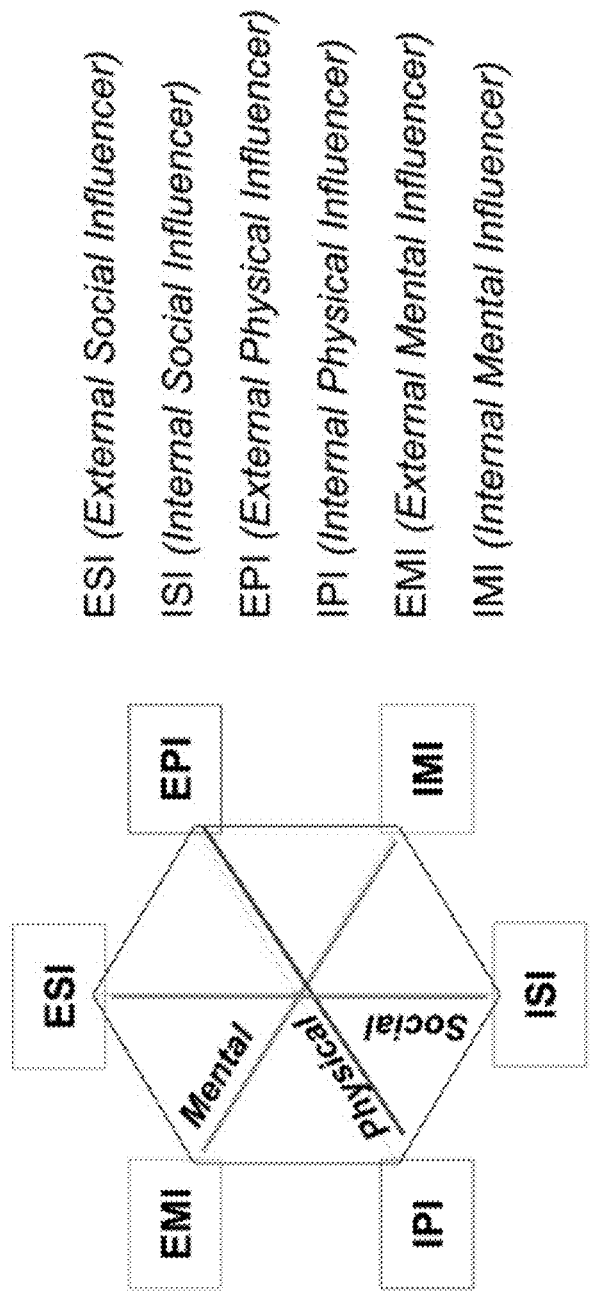
FIG. 6A illustrates six influencers in accordance with one embodiment of the present invention.

Currently, there exists no structured representation of causal factors for emotional wellness. Embodiments of the present invention solve the problem by building a structure to represent six categorical attributes that capture essential elements of causal factors that influence affect. In short, influencers are categorical factors that influence user affect. FIG. 6A illustrates six influencers in accordance with one embodiment of the present invention. The present invention defines six influencer categories: external social influencer (ESI), internal social influencer (ISI), external physical influencer (EPI), internal physical influencer (IPI), external mental influencer (EMI), and internal mental influencer (IMI). Each influencer has negative and positive orientations, making a total of twelve influencers.

External social influencers (ESI) is a categorical factor that involves social experience with the outside world that influence affect. Negative external social influencers (NESI) may include, but are not limited to, bereavement; adverse experience; loss of jobs, friends or family; stress at work, home or school; poor, unstable, or unsafe living conditions; or poor social life. Positive external social influencers (PESI) may include, but are not limited to, positive events in social life; good friends and family; good, safe/stable living conditions; good jobs; or good social life.

Internal social influencers (ISI) is a categorical factor that involves personal and internal attributes that influence affect, as in personality and social coping skills. Negative internal social influencers (NISI) may include, but are not limited to, negative "can't do" attitudes, lack of confidence or motivation, personality that may affect social skills such as perfectionism; poor social coping skills; a poor education; low self-esteem; or impulsive behavior. Positive internal social influencers (PISI) may include, but are not limited to, positive "can do" attitudes, confidence, strong will power and determination to achieve a special goal, a positive personality, good social coping skills, or good education.

External physical influencers (EPI) is a categorical factor that involves physical experience with the outside world that influence affect. Negative external physical influencers (NEPI) may include, but are not limited to, physical abuse and violence; substance abuse (e.g. drugs, alcohol); medication that affects mood; poor nutrition; or poor weather. Positive external physical influencers (PEPI) may include, but are not limited to, sports and exercise, music, balanced diet, good food, hobby, or nice weather.

Internal physical influencers (IPI) is a categorical factor that involves personal and internal attributes that affect physical experience that influence affect. IPI affect you from inside of yourself as in personal and internal physical conditions. Negative internal physical influencers (NIPI) may include, but are not limited to, brain trauma, hunger, stress from illness, illness and injury, poor fitness, lack of sleep, or exhaustion. Positive internal physical influencers (PIPI) may include, but are not limited to, good physical health and fitness.

External mental influencers (EMI) is a categorical factor that involves mental or spiritual experiences with the outside world that influence affect. Negative external mental influencers (NEMI) may include, but are not limited to, emotional abuse, harassment, mental abuse or bullying. Positive external mental influencers (PEMI) may include, but are not limited to, goodwill help by someone or positive spiritual experience.

Internal mental influencers (IMI) is a categorical factor that involves personal and internal attributes that affect mental experience that influence affect. In other words, the IMI affect you from inside or yourself, as in personal and internal mental conditions. Negative internal mental influencers (NIMI) may include, but are not limited to, injury to neural systems, genetics, mental disorders, or biological disorders that affect mood negatively. Positive internal mental influencers (PIMI) may include, but are not limited to, faith and spirituality.

Figure 6B:
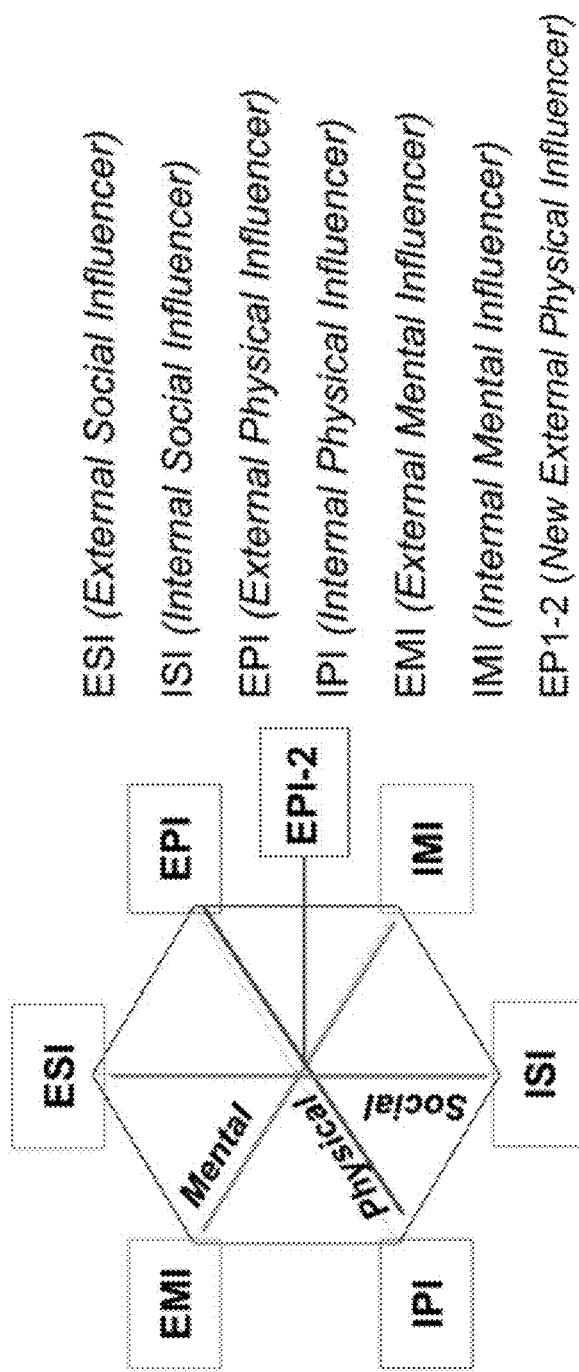
FIG. 6B illustrates adding a seventh influencer in accordance with one embodiment of the present invention.
Figures 7A, 7B:
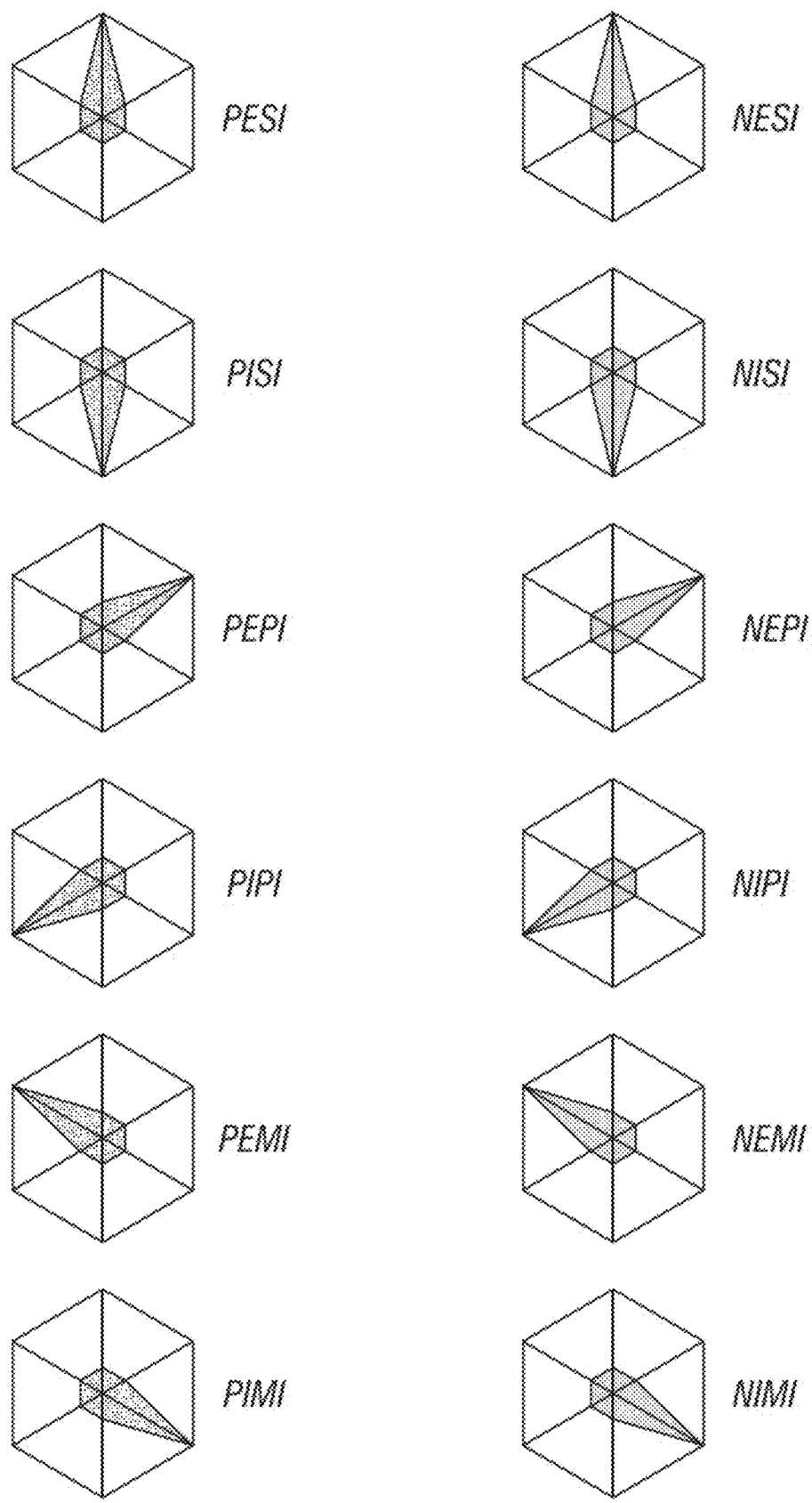
FIGS. 7A and 7B illustrate positive and negative influencers in accordance with embodiments of the present invention.

FIG. 6B illustrates adding a seventh influencer in accordance with one embodiment of the present invention. The number of influencers can be reduced by eliminating one or more influencers and the number of influencers can be increased by adding one or more influencers. As shown in FIG. 6B user influencers can be changed to the appropriate levels of granularity in the user influencer dimension. Typically, EPI represents a large group of external physical influencing factors. When one wishes to capture more information about negative external physical influencer (EPI) regarding physical violence such as violence at home, school, or work, a new EPI dimension can be introduced, for example EPI-2. EPI-2 is a new external physical influencer that specifically represents physical interactions with people. As a result, user can select negative EPI-2 if domestic violence is affecting emotional well-being negatively, for example. Similarly, user can select positive EPI-2 if any physical interactions with people, such as sports, are positively influencing emotional well-being. Because the influencers are broadly categorized, any specific elements within each influencer can be extracted as a subset and represented as a new influencer dimension. Similarly, the number of user activity options can be reduced by eliminating one or more influencers. On the contrary, the number of user activity options can be increased by adding one or more influencers FIG. 7A illustrates positive influencers and FIG. 7B illustrates negative influencers, in accordance with embodiments of the present invention. In FIG. 7A, the light gray area depicts positive influencers including PESI, PISI, PEPI, PIPI, PEMI and PIMI. In FIG. 7B, the dark gray area depicts the negative influencers including NESI, NISI, NEPI, NIPI, NEMI and NIMI. In practice, other colors or patterns to depict the positive and negative influencers may be displayed.

Figures 8A, 8B:
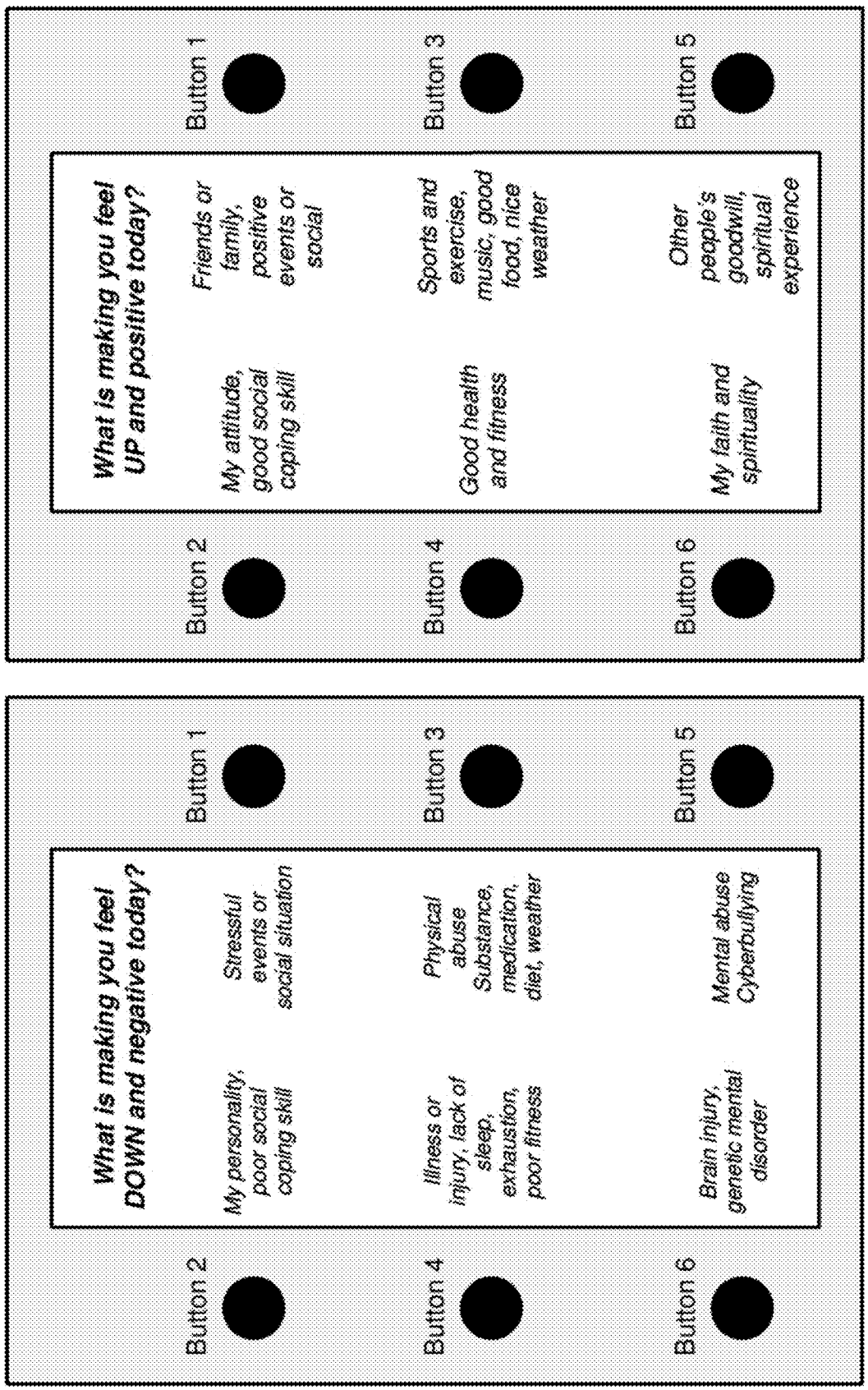
FIGS. 8A and 8B illustrate how the EWMS captures user influencers in accordance with one embodiment of the present invention.

FIGS. 8A and 8B illustrate an example of how the system captures user influencers in accordance with one embodiment of the present invention. There are multiple methods of capturing user influencers. In preferred embodiments of the present invention, the user presses one of six buttons or iconized images on a user interface. FIG. 8A represents a user interface for capturing the negative influencers. FIG. 8B represents a user interface for capturing the positive influencers. The user touches an image or button on the user interface device to select one of six influencers for both negative and positive orientation: ESI, ISI, EPI, IPI, EMI and IMI.

Figure 9:
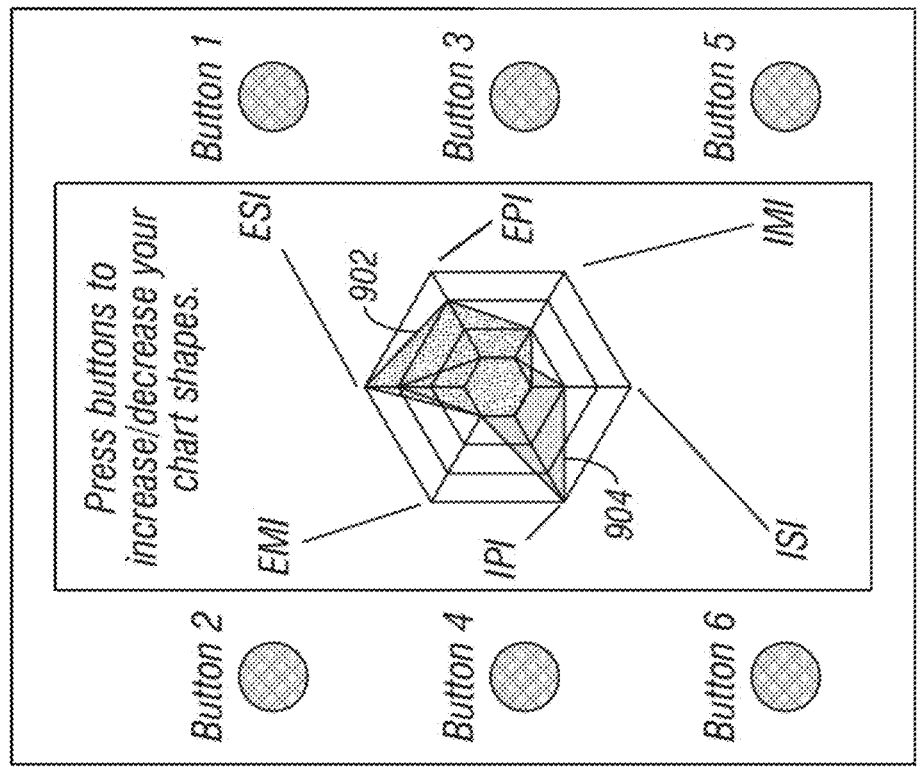
FIG. 9 illustrates how a user enters and edits influencers in accordance with one embodiment of the present invention.

FIG. 9 illustrates how a user can enter and edit influencers directly by pressing one of six buttons in accordance with one embodiment of the present invention on the user interface. The influencer diagram visually represents both the positive and negative influencers at the same time as shown by the overlapping positive influencer chart 902 and the negative influencer chart 904.

Figure 10:
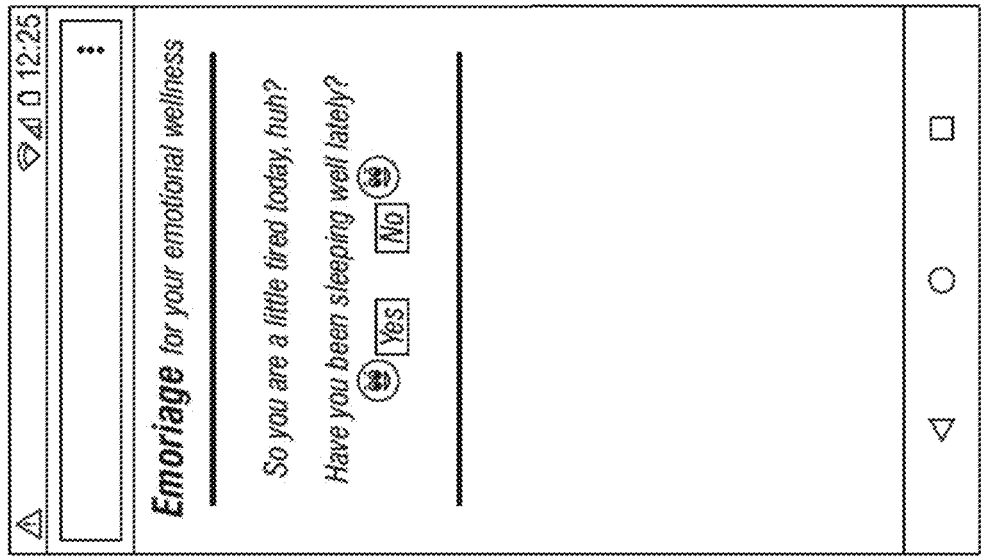
FIG. 10 illustrates yet another user interface to capture influencers in accordance with one embodiment of the present invention.

FIG. 10 illustrates yet another user interface to capture influencers according to one embodiment of the present invention. FIG. 10 shows an interactive decision tree dialog used to capture influencers. This method provides a series of yes or no questions. In other formats, a natural language dialog may be utilized.

Figure 11:
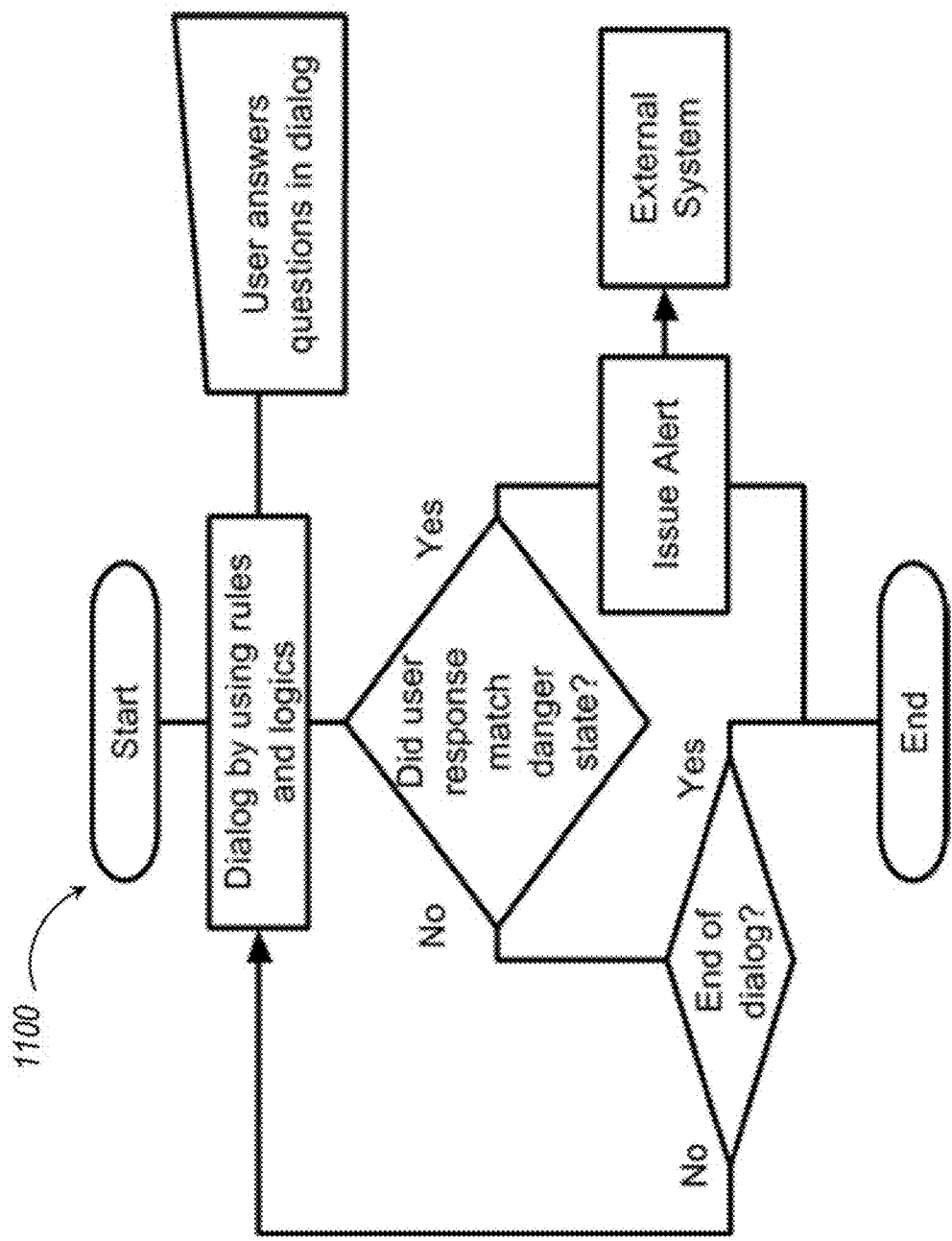
FIG. 11 illustrates a flowchart of how intervention is triggered in accordance with one embodiment of the present invention.

FIG. 11 illustrates a flowchart 1100 of how intervention for a user is triggered, according to an embodiment of the present invention. When decision trees or natural language dialog is used, it is possible to detect suicidal or harmful conditions in user affect and influencers. For example, the flowchart illustrates where the system provides a dialog to the user using rules and logics. The user answers the questions in the dialog. The system will determine whether the user's response matches a danger state. If the user's response matches a danger state then the system will issue an alert to the external system. If the user's response does not match a danger state, then the dialog may end with the system or the system can return to providing more dialog by using rules and logics to the user.

As discussed, emotional wellness is a lifelong process of being aware and making choices. By capturing and visually presenting user affect and influencers, embodiments of the present invention help users become aware of their well-being. In addition, the present invention helps users make an effective choice of actions by connecting users to various support resources. People have traditionally relied on their friends and family members as their support network to help their emotional well-being. Support networks provide people comfort and guidance to make better choices. In today's fast-moving, high-pressure society powered by electronic devices and networks, it is becoming increasingly difficult to build an effective support network.

Figure 12B:
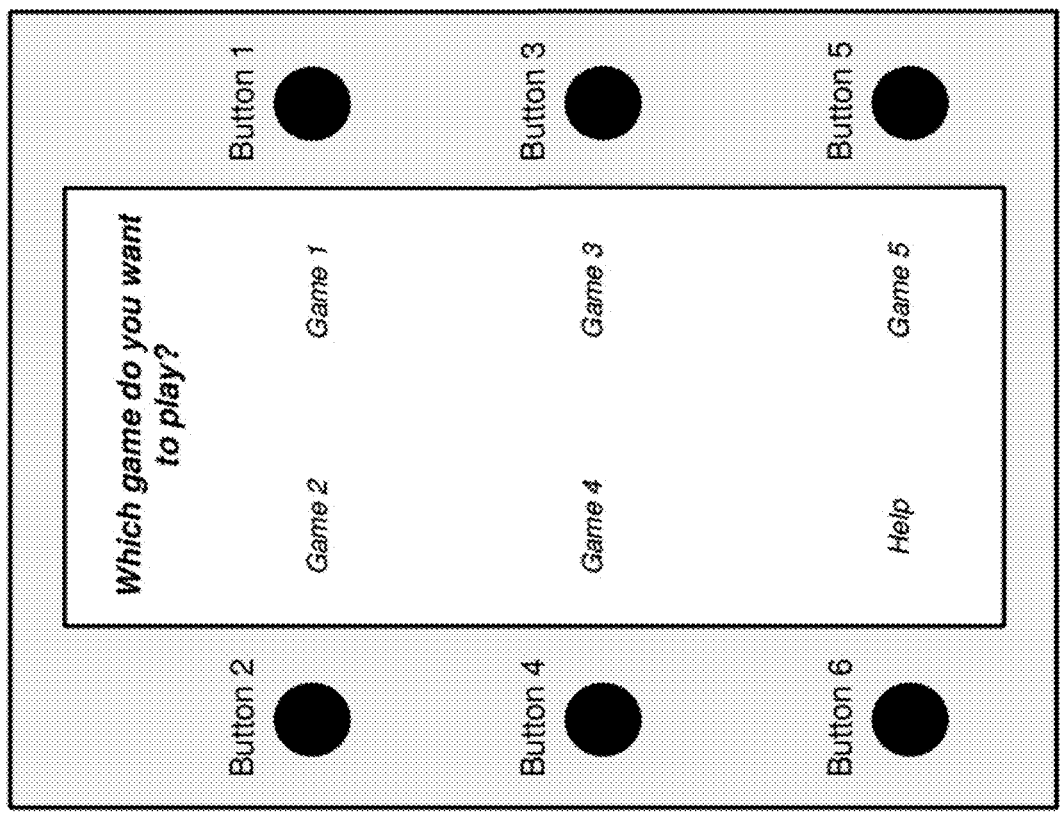
FIGS. 12A and 12B illustrate action links with six buttons in accordance with one embodiment of the present invention.
Figure 12A:
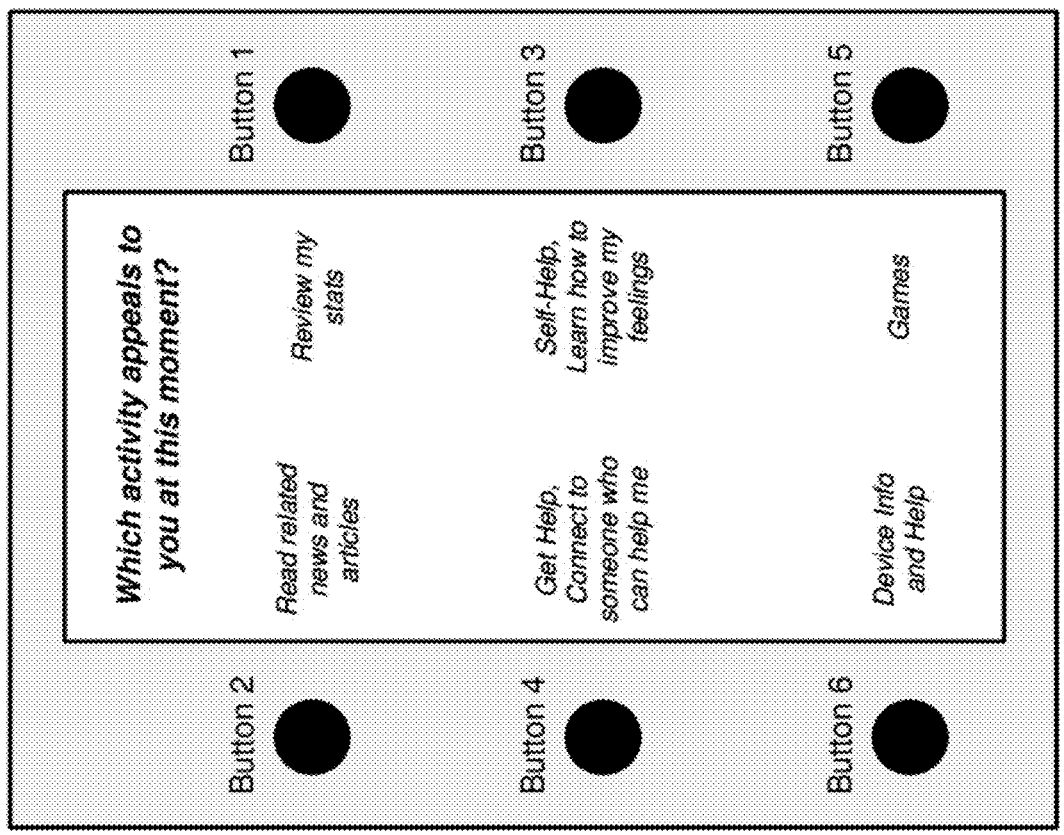

FIGS. 12A and 12B illustrate presenting action links with six buttons on a user interface, according to one embodiment of the present invention. FIG. 12A shows a set of text or images with six buttons, each associated with one of six actions: (1) review my stats, (2) read related news and articles, (3) self-help—learn how to improve my feelings, (4) get help—connect to someone who can help me, (5) games, and (6) device info and help. When the user selects the button 5, for example, a new screen will appear as illustrated in FIG. 12B. This screen shows a set of text or images with six buttons associated with games.

FIGS. 13A-13F show a broader illustration of generated action links with six buttons, according to an embodiment of the present invention. FIG. 13A shows the top level action plan links 26, where each of six buttons or icons is associated with a particular category of activities. The activity categories include, for example, Activity 1 Monitor, Activity 2 Reading, Activity 3 Play, Activity 4 Self-Help, Activity 5 Get-Help and Activity Status. Selecting one of the buttons or icons updates the screen to an associated action link page. In FIG. 13B, the monitor room 27 is a collection of action links to review user statistics and progress of affect, influencers, and activity history. In FIG. 13C, the reading room 28 is a collection of news and articles such as the latest (including online) news on therapies and services. In FIG. 13D, the self-help room 29 is a collection of various self-help activities such as meditation and exercise. In FIG. 13E, the get help room 30 is a collection of communication links to external support providers and systems such as therapists, counseling services and telemedicine systems. In FIG. 13F, the play room 31 is a collection of fun games.

FIG. 14 illustrates a default data structure of user affect 1401, positive influencers 1402, negative influencers 1403, and user activities 1404 in accordance with one embodiment of the present invention. All four data sets share the same number of data slots, three of which (ID, Time Stamp, Counter) are identical. The remaining six data slots correspond to the six elements of affect, influencers and activities.

Figure 15B:
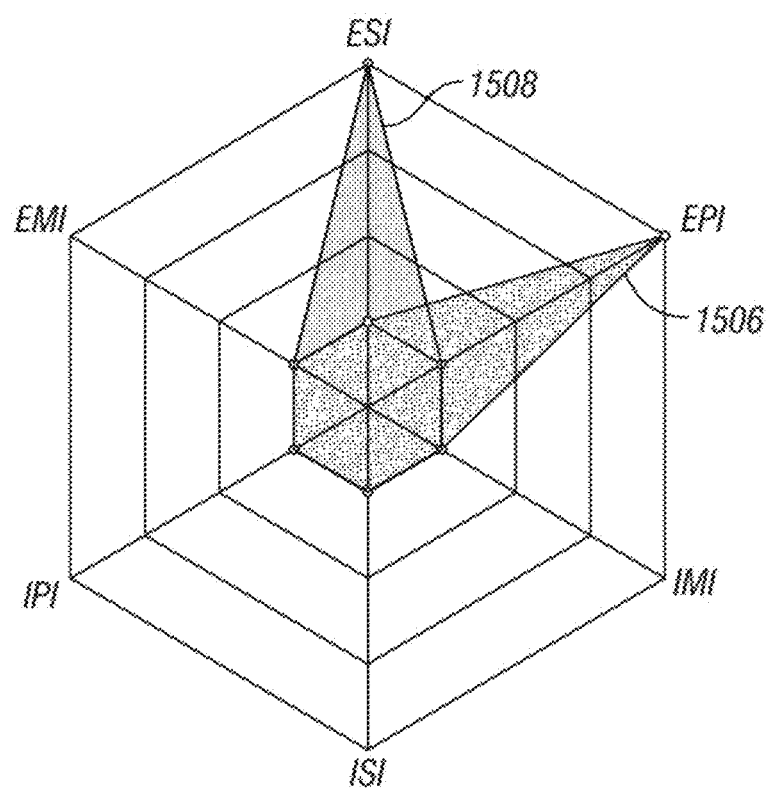

FIG. 15A illustrates the data structure when a new data is captured and FIG. 15B illustrates a visual diagram, according to one embodiment of the present invention. At any given time when user affect is captured, the timestamp is recorded, the counter is incremented by one, and the captured affect state is marked with one as shown in data set 1501 in FIG. 15A. In this particular example, user indicated GLOOMY as the current affect. Similarly, when user influencer is captured for both negative and positive orientations, the timestamp is recorded, the counter is incremented by one, and the captured influencer is marked with one as shown in data sets 1502, 1503 in FIG. 15A. Lastly, when user selects an activity, the time stamp, the counter, and the selected activity slots are updated in data set 1504. In this particular example, user selected a reading activity, perhaps to learn more about the topic.

Based on the captured data, the system can generate a visual diagram of influencers as shown in FIG. 15B. The light gray chart 1506 shows the positive influencer, the dark gray chart 1508 shows the negative influencer. On the user interface device charts, the influencers 1506 and 1508 may be depicted in different colors (e.g. green for positive and red for negative), patterns or other indicators and combinations thereof. In this particular example, the user selected NESI, negative external social influencer, indicating that some social pressure such as work stress is influencing user affect negatively. The selection of PEPI, positive external physical influencer indicates that the user is feeling positive by the influence of some physical elements such as exercise, good weather, or good food.

Figure 16B:
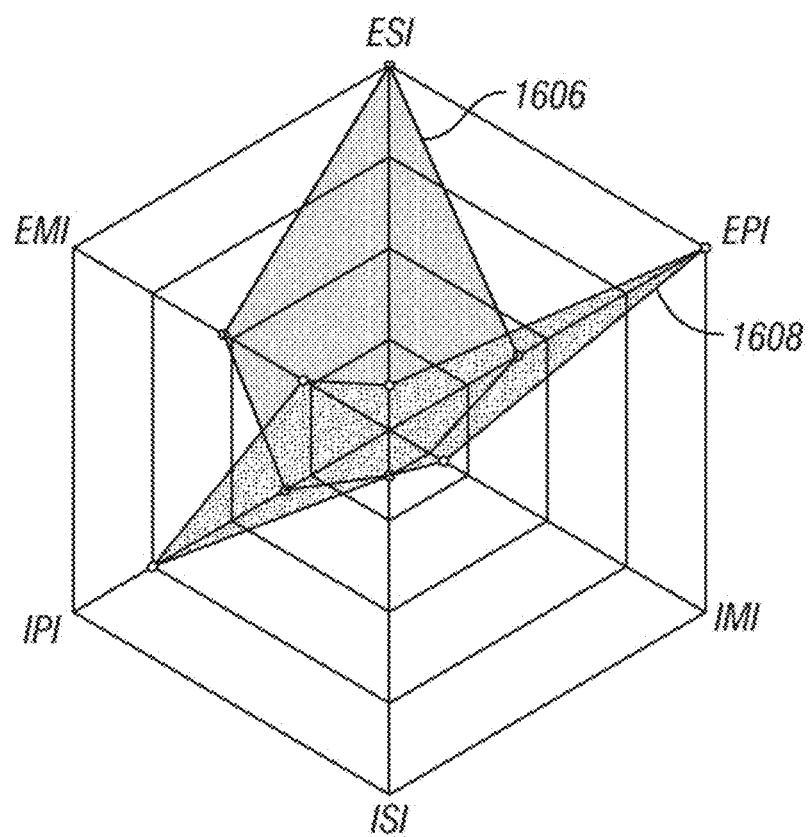

FIG. 16A illustrates the data structure when accumulated data sets for the first 100 entries are captured and FIG. 16B illustrates an influencer diagram according to one embodiment of the present invention. As the user repeats and enters more data in coming days, weeks and months, the system accumulates data. Data can be added in an arbitrary time range for display.

By dividing each of six values by the largest value, a normalized influencer diagram can be generated. For example, the largest value of negative influencers in data set 1602 of FIG. 16A is 40 (NESI); thus dividing each of six values by 40 yields 100% (NESI), 12.5% (NISI), 40.0% (NEPI), 32.5% (NIPI), 52.5% (NEMI), and 12.5% (NIMI). Similarly the largest value of positive influencers in data set 1603 of FIG. 16A is 41 (PEPI), yielding 12.2% (PESI), 12.2% (PISI), 100% (PEPI), 75% (PIPI), 26.8% (PEMI) and 17% (PIMI). Graphing these values in an influencer diagram is shown in FIG. 16B.

In this example, the influencer diagram is showing the user's strong tendency to be affected negatively by external social influencer, followed by external mental influencer (dark gray chart 1606). The graph is also showing the user's strong tendency to feel positive because of both external and internal physical influencers (light gray chart 1608). These shapes imply that the user most often felt social events and situations stressful during this time period, but physical remedies and health helped coping with the negatives. This visualization, otherwise unavailable without this present invention, provides vital feedback to the user.

For example, priorities on recommended activities can be placed on topics such as stress relief, mental abuse, physical fitness, outdoor activities, music, and nutrition. The logic behind this is that this user is feeling down with social situations but some external physical elements and health are making the user feel better. Therefore, such topics as stress relief and fitness may be of the user's interest.

In addition, the activity history in data set 1604 indicates that the user selects "Reading" fairly often (20% of total activities). This implies that the content needs to be fresh and updated to be useful for the user. Content for Self-Help, Get-Help, and Games can also be customized and prioritized based on the similar logic. The exact logic of the priority association between reading materials, affect and influencers should be made customizable at the time of implementation.

Figure 16C:
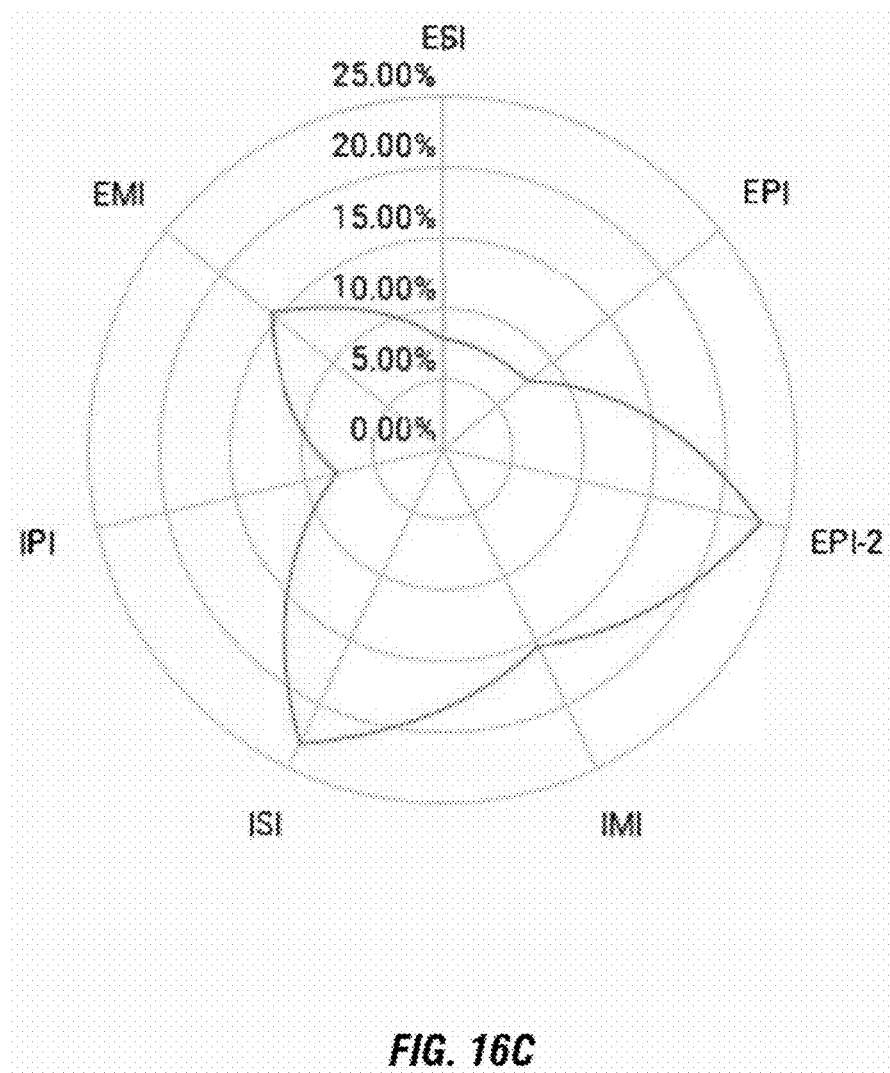
FIG. 16C illustrates graph that reflects the added negative influencers, in accordance with an embodiment of the present invention.

The graph as shown in FIG. 16C illustrates the appropriate dimensional changes in the captured data when there are seven influencers instead of six. FIG. 16C is a visual representation of the dimension change described above. FIG. 16C is an example of a graph with seven influencers that reflect the added state in negative influencer, EPI-2. The new state, EPI-2 is added, making the dimension changed to seven. As described above, EPI typically represents a large group of external physical influencing factors. When one wishes to capture more information about negative external physical influencer regarding physical violence such as violence at home, school, or work, a new EPI dimension can be introduced, for example EP1-2. EPI-2 is a new external physical influencer that specifically represents physical interactions with people. As a result, user can select negative EPI-2 if domestic violence is affecting emotional well-being negatively, for example. Similarly, user can select positive EPI-2 if any physical interactions with people, such as sports, are positively influencing emotional well-being. Because the influencers are broadly categorized, any specific elements within each influencer can be extracted as a subset and represented as a new influencer dimension.

Figure 17G:
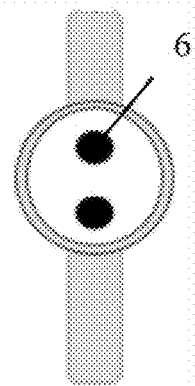
FIGS. 17G-17N illustrates the number of interactive interfaces being customizable in accordance with embodiments of the present invention.

FIGS. 17A-17F illustrates various form factors of a six-button device in accordance with embodiments of the present invention. As shown and described, alternative forms of a device with six buttons can capture six essential states of user affect, capture six essential attributes of user influencers, and provide a series of six action links to complete the feedback mechanism for emotional wellness. For example, FIGS. 17A and 17B illustrate varying configurations of the display windows and buttons. The device can be in the form of a box, hexagon, cube, inline (see FIGS. 17C, 17D 17E, and 17F). As illustrated in FIGS. 17C-17G, the device can be implanted into belts, bracelets, other wearable objects, dice, mobile devices, iPads, or toys. As evident from the structured representation of user affect, influencers and actions, an embodiment of the present invention requires only six buttons to perform the complete operation.

Figure 18:
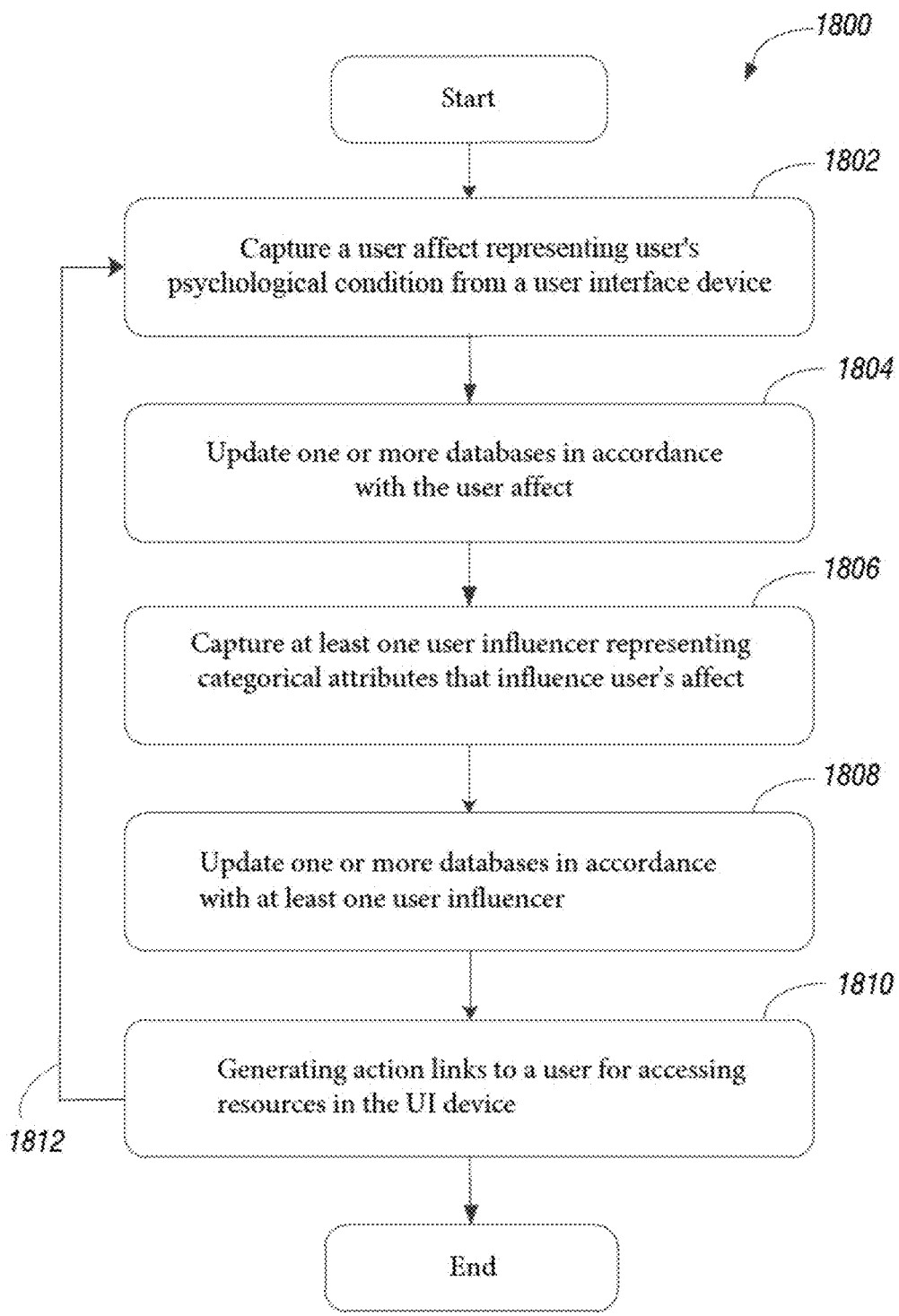
FIG. 18 is a flowchart illustrating an exemplary process to obtain a desired state of emotional wellness, according to an embodiment of the present invention.

FIG. 18 illustrates the method of managing emotional wellness in a system 1800 having a processor/controller and a storage/memory, in accordance with an exemplary process of the present invention. At step 1802, the system captures at least one user affect representing the user's psychological condition from a user interface device. Capturing the at least one user affect includes receiving signals representing the user's condition from the user interface device. At step 1804, the system updates one more databases in accordance with the user affect. At step 1806, the system captures at least one user influencer representing categorical attributes that influence user's affect. Capturing the at least one user influencer includes receiving signals representing user information from the categorical attributes sent by the user. At step 1808, the system updates one or more databases in accordance with the user influencer. At step 1810, the system generates and displays action links to a user for accessing resources in the user interface device. The action links are customized links to various content, services and people in response to the one or more databases updated with captured affect and influencers. The process iterates 1812 until a desired state of emotionally wellness is obtained.

Moreover, an embodiment of the invention is directed to an article of manufacture for use in a digital processing system for managing emotional wellness, where the article of manufacture comprises a digital processing system usable medium having readable program code embodied in the medium, and the program code comprising the aforementioned method steps as depicted in FIG. 18. The steps of the exemplary process may be embodied in machine, router or computer executable instructions. The instructions can be used to create a general purpose or special purpose system, which is programmed with the instructions, to perform the steps of the exemplary process of the present invention. Alternatively, the steps may be performed by specific hardware components that contain hard-wired-logic for performing the steps, or by any combination of programmed computer components and custom hardware components. As such, embodiments of the present invention may be implemented as software, configured for use in commonly available computing devices and configured to interface with external devices. This system can be used as a standalone system without network, or a networked system to serve multiple users simultaneously over multiple communication channels.

Figure 17H:
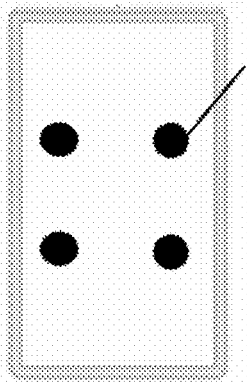
Figure 17I:
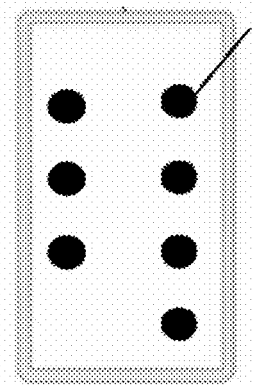
Figure 17J:
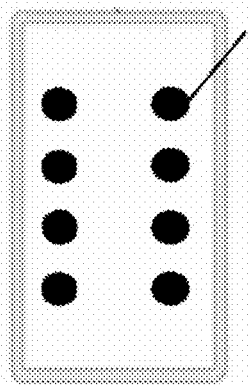

FIGS. 17G-17N illustrates the number of interactive interface 6 being customizable in accordance with embodiments of the present invention. Each embodiment illustrated can be altered in order to support the number of user affect and influencers. As illustrated in FIG. 17G, there is a wearable device, where the quantity of the interactive interface 6 can be two. As illustrated in FIG. 17H, there is a handheld device where the quantity of the interactive interface 6 can be at least four. As illustrated in FIG. 17I, there is another handheld device where the quantity of the interactive interface 6 can be at least seven. As illustrated in FIG. 17J, there is another handheld device where the quantity of the interactive interface 6 can be at least eight.

Figure 17K:
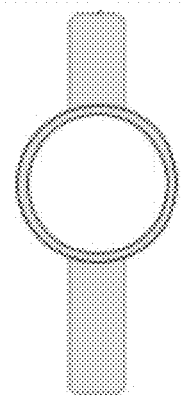
Figure 17L:
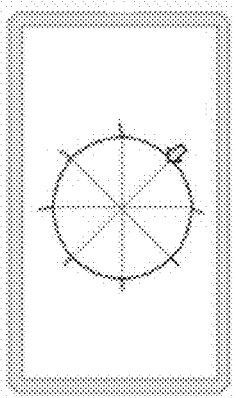
Figure 17M:
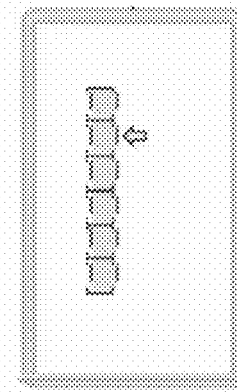
Figure 17N:
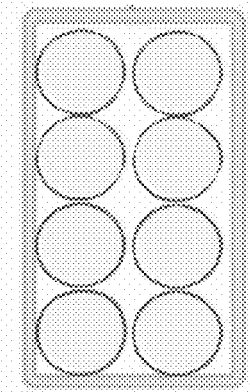

The system and methods of capturing user affect and influencers can occur beyond buttons. As illustrated in FIGS. 17K-17N, instead of using buttons, the system can utilize other interactive interfaces 6 such as dials, slider bars, and touch inputs, while other embodiments can also be contemplated. As illustrated in FIG. 17K a dial, slide, touch inputs can be used for wearable devices. As illustrated in FIG. 17L a dial input can be used for handheld devices. As illustrated in FIG. 17M slide input can be used for handheld devices. As illustrated in FIG. 17N touch input can be used for handheld devices.

By changing the quantity of the interactive interface 6 and changing the type of interactive interface 6 i.e., dials, slider bars, buttons, or touch inputs, it allows for flexibility in the embodiments. Another way to increase the flexibility in the embodiments is to change the display type of the captured user affect and influencers. The display type can be a variety of graph types as well as text.

Figure 19:
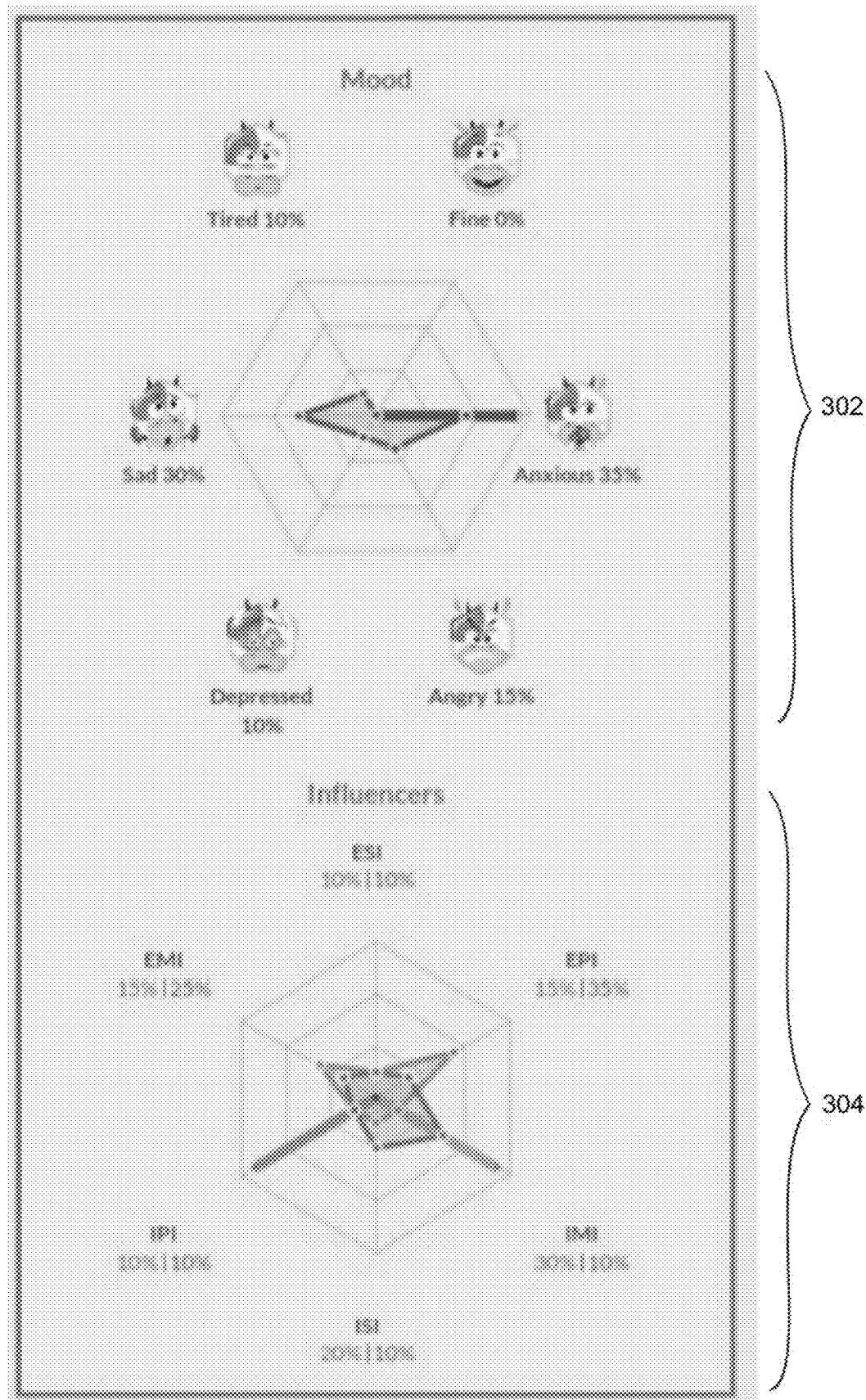
FIG. 19 illustrates two graphs containing information about the user's affect and influencer history in accordance with embodiments of the present invention.

FIG. 19 illustrates a mood distribution graph 302 and an influencer distribution graph 304 containing information about the user's affect and influencer history in accordance with embodiments of the present invention. The graphs comprise useful information but unless users know how to interpret them, it is often difficult to understand what the graphs truly mean. Without prior knowledge or help, users do not appreciate the displayed graphs. This is especially problematic when a physician, as a support network, tries to help a patient with EWMS 4 data but does not understand the meaning of the graphs shown in the patient's EWMS 4. Therefore, an auto-narrative function can be used to solve this issue.

An auto-narrative function converts graph data into text data. This function helps users understand what the graph means. For example, the user sees a graph on the screen, touches a help button, and sees a new page with details and meanings of the graph in descriptive text. With the text data, the user can read and understand what the graphs mean without any prior knowledge of the graphs.

The auto-narrative function consists of a template and graph data values. As illustrated in FIG. 19 there are two graphs shown: one is a mood distribution 302 and the other is an influencer distribution 304. These two graphs contain valuable information about the user's affect and influencer history. It is possible to parameterize the values of the graphs as shown in FIG. 19 by creating a text template.

TABLE 1

Text Template

Key Indication

The graphs are showing that you've been feeling name_topmood most often (val_topmood%) over the recorded period. Your risk factors that make you feel negative often are name_topni (val_topni%), which could include desc_topni. Your protective factors that help you feel positive often are name_toppi (val_toppi%), which could include desc_toppi.

Detail About Your Graphs

The top graph is your mood distributions that indicate your emotional well-being. Over the recorded period, your mood was "Fine" val_fin%, "Tired" val_tir%, "Anxious" val_anx%, "Sad" val_sad%, "Angry" val_ang%, and "Depressed" val_dep%. The dark blue bar indicates the last entry of your mood, which is name_lastmood.

The bottom graph is your influencer distributions that indicate your risk and protective factors for your emotional well-being. Over the recorded period, your risk factors (shown in red color) were ESI (external social influencer) val_nesi%, ISI (internal social influencer) val_nisi%, EPI (external physical influencer) val_nepi%, IPI (internal physical influencer) val_nipi%, EMI (external mental influencer) val_nemi%, and IMI (internal mental influencer) val_nimi%. The dark red bar indicates the last entry of your negative influencer, which is name_lastni.

Your protective factors (shown in green color) were ESI (external social influencer) val_pesi%, ISI (internal social influencer) val_pisi%, EPI (external physical influencer) val_pepi%, IPI (internal physical influencer) val_pipi%, EMI (external mental influencer) val_pemi%, and IMI (internal mental influencer) val_pimi%. The dark green bar indicates the last entry of your positive influencer, which is name_lastpi.

The words in bold italic as shown in Table 1 can have specific variables in the graphs, as shown in Table 2.

TABLE 2

| | Specific Variables of Graph |
|---|---|
| val_fin | percent value of mood Fine |
| val_tir | percent value of mood Tired |
| val_anx | percent value of mood Anxious |
| val_sad | percent value of mood Sad |
| val_ang | percent value of mood Angry |
| val_dep | percent value of mood Depressed |
| name_lastmood | name of the last mood entry = {Fine, Tired, Anxious, Sad, Angry, Depressed} |
| val_topmood | the highest percent value among all mood types, which can be: val_fin, val_tir, val_anx, val_sad, val_ang, val_dep (more than one "top" value is possible) |
| name_topmood | name of the top mood with val_topmood (more than one "top" name is possible) |
| val_nesi | percent value of negative external social influencer (NESI) |
| val_nisi | percent value of negative internal social influencer (NISI) |
| val_nepi | percent value of negative external physical influencer (NEPI) |
| val_nipi | percent value of negative internal physical influencer (NIPI) |
| val_nemi | percent value of negative external mental influencer (NEMI) |
| val_nimi | percent value of negative internal mental influencer (NIMI) |
| desc_nesi | "poor social life, stress at work, home or school, bereavement, and poor living conditions" |
| desc_nisi | "negative 'can't do' attitudes, poor social coping skills, low self-esteem, and lack of confidence or motivation" |
| desc_nepi | "physical abuse and violence, substance abuse, medication that affects mood, poor nutrition, and poor weather" |

TABLE 2-continued

Specific Variables of Graph

| Variable | Description |
|---|---|
| desc_nipi | "stress from illness, injury, or poor fitness, lack of sleep, or exhaustion" |
| desc_nemi | "emotional abuse, harassment, or bullying by someone" |
| desc_nimi | "biological disorders that affect mood negatively" |
| name_lastni | name of the last negative influencer entry = {External Social Influencer, Internal Social Influencer, External Physical Influencer, Internal Physical Influencer, External Mental Influencer, Internal Mental Influencer} |
| val_topni | the highest percent value among all negative influencers; max(val_nepi, val_nisi, val_nepi, val_nipi, val_nemi, val_nimi) (More than one "top" values are possible) |
| name_topni | name of the top negative influencer with val_topni = {External Social Influencer, Internal Social Influencer, External Physical Influencer, Internal Physical Influencer, External Mental Influencer, Internal Mental Influencer} (More than one "top" names are possible) |
| desc_topni | description of the top negative influencer = {desc_nesi, desc_nisi, desc_nepi, desc_nipi, desc_nemi, desc_nimi} (More than one "top" descriptions are possible) |
| val_pesi | percent value of positive external social influencer (PESI) |
| val_pisi | percent value of positive internal social influencer (PISI) |
| val_pepi | percent value of positive external physical influencer (PEPI) |
| val_pipi | percent value of positive internal physical influencer (PIPI) |
| val_pemi | percent value of positive external mental influencer (PEMI) |
| val_pimi | percent value of positive internal mental influencer (PIMI) |
| desc_pesi | "positive events in social life, good friends and family, and good living conditions" |
| desc_pisi | "positive 'can do' attitudes, good social coping skills, confidence, and strong will power and determination to achieve a special goal" |
| desc_pepi | "exercise, sports, music, good food, hobby, and nice weather" |
| desc_pipi | "good physical health and fitness" |
| desc_pemi | "goodwill help by someone or positive spiritual experience" |
| desc_pimi | "faith and spirituality" |
| name_lastpi | name of the last positive influencer entry = {External Social Influencer, Internal Social Influencer, External Physical Influencer, Internal Physical Influencer, External Mental Influencer, Internal Mental Influencer} |
| val_toppi | the highest percent value among all positive influencers; max(val_pepi, val_pisi, val_pepi, val_pipi, val_pemi, val_pimi) More than one "top" values are possible. |
| name_toppi | name of the top positive influencer with val_toppi = {External Social Influencer, Internal Social Influencer, External Physical Influencer, Internal Physical Influencer, External Mental Influencer, Internal Mental Influencer} (More than one "top" names are possible) |
| desc_toppi | description of the top positive influencer = {desc_pesi, desc_pisi, desc_pepi, desc_pipi, desc_pemi, desc_pimi} (More than one "top" descriptions are possible) |

TABLE 3

Actual Values in Mood Graph and Influencers Graph Illustrated in FIG. 19

| Variable | Value |
|---|---|
| val_fin | 0 |
| val_tir | 10 |
| val_anx | 35 |
| val_sad | 30 |
| val_ang | 15 |
| val_dep | 10 |
| name_lastmood | Anxious |
| val_topmood | 35 |
| name_topmood | Anxious |
| val_nesi | 10 |
| val_nisi | 10 |
| val_nepi | 35 |
| val_nipi | 10 |
| val_nemi | 25 |
| val_nimi | 10 |
| desc_nesi | "poor social life, stress at work, home or school, bereavement, and poor living conditions" |
| desc_nisi | "negative 'can't do' attitudes, poor social coping skills, low self-esteem, and lack of confidence or motivation" |
| desc_nepi | "physical abuse and violence, substance abuse, medication that affects mood, poor nutrition, and poor weather" |
| desc_nipi | "stress from illness, injury, or poor fitness, lack of sleep, or exhaustion" |
| desc_nemi | "emotional abuse, harassment, or bullying by someone" |
| desc_nimi | "biological disorders that affect mood negatively" |
| name_lastni | Internal Physical Influencer |
| val_topni | 35 |
| name_topni | External Physical Influencer |
| desc_topni | "physical abuse and violence, substance abuse, medication that affects mood, poor nutrition, and poor weather" |
| val_pesi | 10 |
| val_pisi | 20 |
| val_pepi | 15 |
| val_pipi | 10 |
| val_pemi | 15 |
| val_pimi | 30 |
| desc_pesi | "positive events in social life, good friends and family, and good living conditions" |
| desc_pisi | "positive 'can do' attitudes, good social coping skills, confidence, and strong will power and determination to achieve a special goal" |
| desc_pepi | "exercise, sports, music, good food, hobby, and nice weather" |
| desc_pipi | "good physical health and fitness" |
| desc_pemi | "goodwill help by someone or positive spiritual experience" |
| desc_pimi | "faith and spirituality" |
| name_lastpi | Internal Mental Influencer |
| val_toppi | 30 |
| name_toppi | Internal Mental Influencer |
| desc_toppi | "faith and spirituality" |

TABLE 4

Comparison Between Text Template and Filled-In Text

| Key Indication Text Template | Key Indication Filled-In Text |
| --- | --- |
| The graphs are showing that you've been feeling name_topmood most often (val_topmood%) over the recorded period. Your risk factors that make you feel negative often are name_topni (val_topni%), which could include desc_topni. Your protective factors that help you feel positive often are name_toppi (val_toppi%), which could include desc_toppi. | The graphs are showing that you've been feeling Anxious most often (35%) over the recorded period. Your risk factors that make you feel negative often are External Physical Influencer (35%), which could include physical abuse and violence, substance abuse, medication that affects mood, poor nutrition, and poor weather. Your protective factors that help you feel positive often are External Mental Influencer (30%), which could include faith and spirituality. |
| Detail About Your Graphs | Details About Your Graphs |
| The top graph is your mood distributions that indicate your emotional well-being. Over the recorded period, your mood was "Fine" val_fin%, "Tired" val_tir%, "Anxious" val_anx%, "Sad" val_sad%, "Angry" val_ang%, and "Depressed" val_dep%. The dark blue bar indicates the last entry of your mood, which is name_lastmood. The bottom graph is your influencer distributions that indicate your risk and protective factors for your emotional well-being. Over the recorded period, your risk factors (shown in red color) were ESI (external social influencer) val_nesi%, ISI (internal social influencer) val_nisi%, EPI (external physical influencer) val_nepi%, IPI (internal physical influencer) val_nipi%, EMI (external mental influencer) val_nemi%, and IMI (internal mental influencer) val_nimi%. The dark red bar indicates the last entry of your negative influencer, which is name_lastni. Your protective factors (shown in green color) were ESI (external social influencer) val_pesi%, ISI (internal social influencer) val_pisi%, EPI (external physical influencer) val_pepi%, IPI (internal physical influencer) val_pipi%, EMI (external mental influencer) val_pemi%, and IMI (internal mental influencer) val_pimi%. The dark green bar indicates the last entry of your positive influencer, which is name_lastpi. | The top graph is your mood distributions that indicate your emotional well-being. Over the recorded period, your mood was "Fine" 0%, "Tired" 10%, "Anxious" 35%, "Sad" 30%, "Angry" 15%, and "Depressed" 10%. The dark blue bar indicates the last entry of your mood, which is Anxious. The bottom graph is your influencer distributions that indicate your risk and protective factors for your emotional well-being. Over the recorded period, your risk factors (shown in red color) were ESI (external social influencer) 10%, ISI (internal social influencer) 10%, EPI (external physical influencer) 35%, IPI (internal physical influencer) 10%, EMI (external mental influencer) 25%, and IMI (internal mental influencer) 10%. The dark red bar indicates the last entry of your negative influencer, which is Internal Physical Influencer. Your protective factors (shown in green color) were ESI (external social influencer) 10%, ISI (internal social influencer) 20%, EPI (external physical influencer) 15%, IPI (internal physical influencer) 10%, EMI (external mental influencer) 15%, and IMI (internal mental influencer) 30%. The dark green bar indicates the last entry of your positive influencer, which is External Mental Influencer. |

Figure 20:
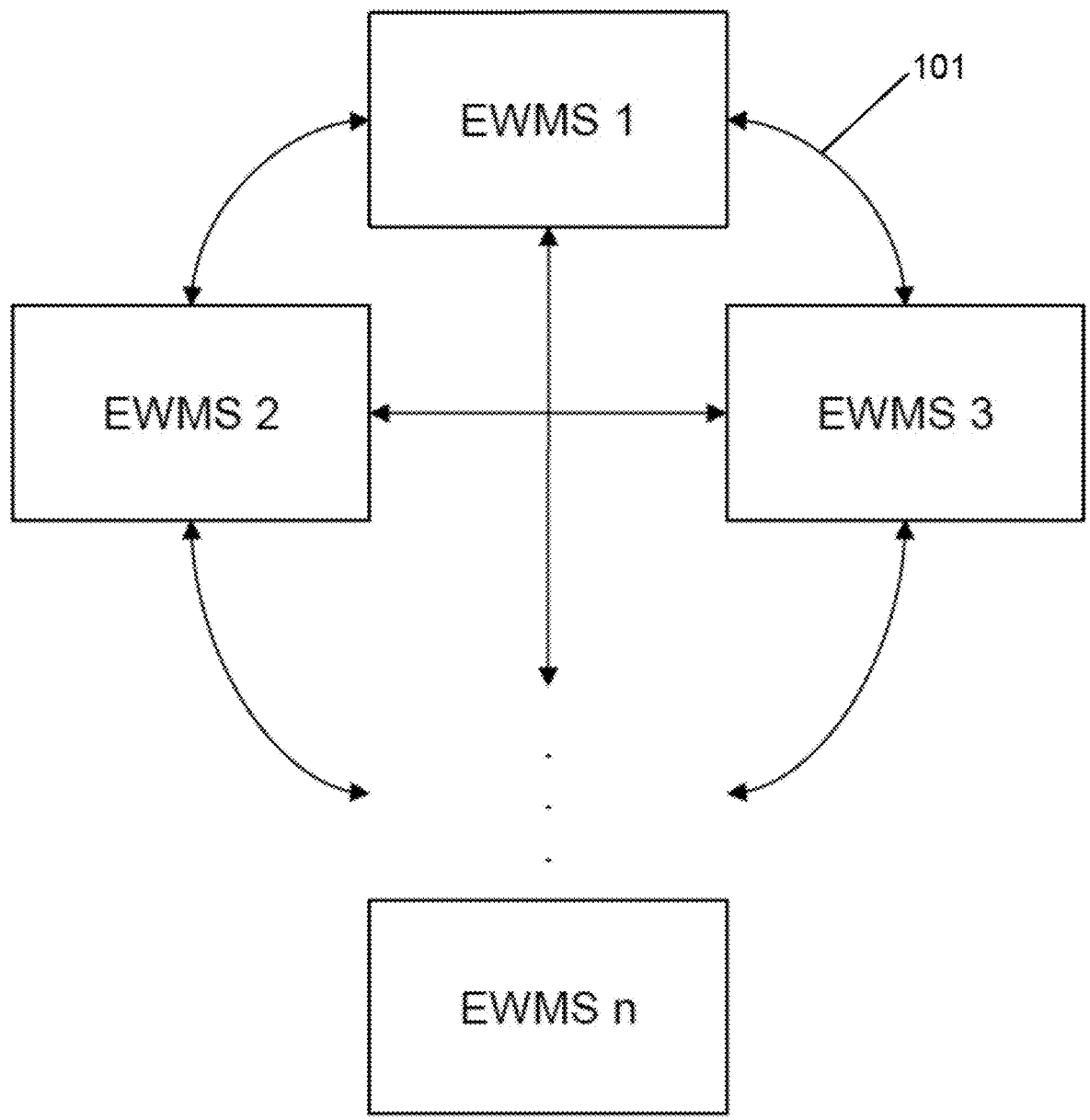
FIG. 20 illustrates more than one device storing data and the system communication links are how the devices interact with each other, according to an embodiment of the present invention.

As shown in FIG. 20, transferring and sharing of the captured data can occur between multiple EWMS 4 devices. More than one electronic device can hold the data. Arrows in FIG. 20 indicate system communication links 101. For example, suppose that EWMS 1 holds data. "n" represents the possible number of EWMS devices existing with or without data. EWMS 1 can send its data to any arbitrary number of EWMS devices to share the data by way of communication links 101.

Throughout the description and drawings, example embodiments are given with reference to specific configurations. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments or alternatives of the foregoing description.

What is claimed is:

1. An iterative emotional wellness management system comprising:
 a user controller able to capture, store, retrieve, process, update and display information related to and comprising user affect, user influencers, and actions;
 a user storage coupled to the user controller and configured to have a user affect database, user influencer database and a user activity database;
 a user interface ("UI") device coupled to the user controller and configured to have a plurality of interactive interfaces to capture user inputs of a plurality of states of user affect and user influencers, and to provide a plurality of action links;
 wherein at least one user affect captured from the UI device represents a psychological condition of the user and the at least one user affect is comprised of both a mood level and an energy level which define the state of the at least one user affect;

wherein the user controller, in response to user inputs of at least one of a plurality of states of user affect and user influencers, hereinafter session data, stores the session data; retrieves the session data and generates a graphical influencer diagram comprising an overlapping user positive influencer chart and user negative influencer chart over a predefined period of time, after the user enters the user influencers; and generates the plurality of action links in accordance with one or more databases; and a support network comprising at least one support network controller able to capture, store, retrieve, process, update and display information related to and comprising user affect, user influencers, and actions of the user;

wherein the user controller and the at least one support network controller transfers or shares information related to and comprising user affect, user influencers, and actions; and an auto-narrative function converts the graphical influencer diagram and a user affect diagram to text data on the UI device.

2. The system of claim 1, wherein each user affect is comprised of both a mood level and an energy level which define the state of the user affect.

3. The system of claim 1, wherein the plurality of interactive interfaces is a dial, a slide bar, and a touch input.

4. The system of claim 1, wherein the auto-narrative function comprises a template and graph data values.

5. The system of claim 1, wherein the user controller transfers or shares information with the at least one support network controller by way of a communication link.

6. The system of claim 5, wherein the communication link is Bluetooth, near-field communication, infrared or radio frequency.

7. The system of claim 1, further comprising the at least one support network controller transferring and sharing captured data with other support network controllers by way of a communication link.

8. The system of claim 1, wherein the interactive interfaces are located on a wearable device.

9. The system of claim 1, wherein the interactive interfaces are located on a handheld device.

10. A method of managing emotional wellness in a system comprising a user interface ("UI") device, a user storage and a user controller, said method comprising:
a) capturing at least one user affect at least partially representing user's psychological condition from the UI device, wherein the at least one user affect is comprised of both a mood level and an energy level which define a state of the at least one user affect;
b) updating one or more databases in accordance with the at least one user affect;
c) capturing at least one user influencer at least partially representing categorical attributes that influence user's affect from the UI device;
d) updating one or more databases in accordance with the at least one user influencer;
e) generating and displaying on the UI device a graphical user affect diagram and a graphical influencer diagram comprising an overlapping positive influencer chart and negative influencer chart representing user influencers over a predefined period of time;
f) connecting to at least one other UI device in a support network;
g) generating action links to the user for accessing resources in the UI device in response to the one or more databases; and
h) iterating steps a) through g) to obtain a desired state of emotional wellness.

11. The method of claim 10, further comprising converting the graphical influencer diagram to text data using an auto-narrative function.

12. The method of claim 10, further comprising converting the graphical user affect diagram to text data using an auto-narrative function.

13. The method of claim 11, wherein converting the graphical influencer diagram comprises parameterizing values of the graphical influencer diagram.

14. The method of claim 12, wherein converting the graphical user affect diagram comprises parameterizing values of the graphical user affect diagram.

15. The method of claim 10, wherein connecting to at least one other UI device in a support network is via a communication link.

16. The method of claim 10, further comprising connecting a plurality of the UI devices in a support network via a communication link.

17. The method of claim 10, wherein capturing the at least one user affect includes receiving signals representing a user condition from a device comprising a plurality of interactive interfaces.

18. The method of claim 10, wherein capturing the at least one user influencer includes receiving signals representing user information from a device comprising a plurality of interactive interfaces.

19. An article of manufacture for use in a digital processing system for managing emotional wellness, the article of manufacture comprising a digital processing system usable medium having readable program code embodied in the medium, the program code comprising:
a) capturing at least one user affect at least partially representing user's psychological condition from a user interface ("UI") device, wherein the at least one user affect is comprised of both a mood level and an energy level which define a state of the at least one user affect;
b) updating one or more databases in accordance with the at least one user affect;
c) capturing at least one user influencer at least partially representing categorical attributes that influence user's affect from the UI device;
d) updating one or more databases in accordance with the at least one user influencer;
e) generating and displaying on the UI device a graphical influencer diagram comprising an overlapping positive influencer chart and negative influencer chart representing user influencers over a predefined period of time;
f) connecting to at least one other UI device in a support network;
g) generating and displaying action links to the user for accessing resources in the UI device in response to the one or more databases; and
h) iterating steps a) through g).

20. The article of claim 19, wherein the graphical influencer diagram is converted to text data.

* * * * *